(12) United States Patent
Jarman et al.

(10) Patent No.: US 10,331,667 B2
(45) Date of Patent: Jun. 25, 2019

(54) SYSTEMS AND METHODS FOR BI-DIRECTIONAL DATABASE APPLICATION PROGRAMMING INTERFACE, EXTRACT TRANSFORM AND LOAD SYSTEM, AND USER COMPUTING DEVICE

(71) Applicant: Hart, Inc., Costa Mesa, CA (US)

(72) Inventors: Ben M. Jarman, Irvine, CA (US); Hoa V. Ho, Ho Chi Minh (VN); Ty H. Hoang, Irvine, CA (US); Mohamed Alkady, Orange, CA (US); Peter A. Tariche, Irvine, CA (US)

(73) Assignee: Hart, Inc., Costa Mesa, CA (US)

( * ) Notice: Subject to any disclaimer, the term of this patent is extended or adjusted under 35 U.S.C. 154(b) by 0 days.

(21) Appl. No.: 15/663,557

(22) Filed: Jul. 28, 2017

(65) Prior Publication Data
US 2018/0032573 A1    Feb. 1, 2018

Related U.S. Application Data

(60) Provisional application No. 62/368,981, filed on Jul. 29, 2016, provisional application No. 62/380,965, (Continued)

(51) Int. Cl.
*G06F 17/30* (2006.01)
*G06F 16/2453* (2019.01)
(Continued)

(52) U.S. Cl.
CPC .... *G06F 16/24534* (2019.01); *G06F 16/3331* (2019.01); *G06F 16/9535* (2019.01)

(58) Field of Classification Search
None
See application file for complete search history.

(56) References Cited

U.S. PATENT DOCUMENTS

| 6,014,670 A | 1/2000 | Zamanian et al. |
| 6,343,295 B1 | 1/2002 | Macleod et al. |
| (Continued) | | |

FOREIGN PATENT DOCUMENTS

AU    2015/227464 A1    10/2015

OTHER PUBLICATIONS

Genesys Telecommunications Laboratories, Inc., Genesys Info Mart 8.1: Deployment Guide, https://genesys.secure.force.com/support/servlet/fileField?id=0BEU0000000TVhF, retrieved on Aug. 8, 2017, from the Nov. 25, 2016 wayback machine capture (https://web.archive.org/web/20161125122522/https://genesys.secure.force.com/support/servlet/fileField?id=0BEU0000000TVhF) (490 pages).

*Primary Examiner* — Tuankhanh D Phan
(74) *Attorney, Agent, or Firm* — Knobbe, Martens, Olson & Bear, LLP

(57) ABSTRACT

Systems and methods are provided for improved integration between database systems. Data from multiple disparate computing systems is transmitted via bi-directional communication interfaces. The data is stored in its original form from respective data sources and transformed in stream and/or batch processes into one or more predefined formats. Individual transformations are stored and/or recorded. The transformed and/or integrated data is provided to one or more computing devices via the communication interfaces.

17 Claims, 40 Drawing Sheets

Related U.S. Application Data filed on Aug. 29, 2016, provisional application No. 62/433,708, filed on Dec. 13, 2016.

(51) Int. Cl.
*G06F 16/9535* (2019.01)
*G06F 16/33* (2019.01)

(56) References Cited

U.S. PATENT DOCUMENTS

| | | |
|---|---|---|
| 7,233,938 B2 | 6/2007 | Carus et al. |
| 8,060,553 B2 | 11/2011 | Mamou et al. |
| 8,452,636 B1 | 5/2013 | Verastigui |
| 8,775,218 B2 | 7/2014 | Burgoon et al. |
| 9,158,827 B1 | 10/2015 | Vu |
| 9,430,114 B1 | 8/2016 | Dingman et al. |
| 2005/0203892 A1 | 9/2005 | Wesley et al. |
| 2014/0032617 A1* | 1/2014 | Stanfill ............. G06F 17/30557 707/809 |
| 2016/0171237 A1 | 6/2016 | Antic et al. |
| 2016/0180033 A1* | 6/2016 | Rosenberg ............ G06F 19/327 705/2 |
| 2017/0109418 A1* | 4/2017 | Bartlett ............. G06F 17/30563 |

\* cited by examiner

| | | |
|---|---|---|
| GET | /medication | Get a user's medication objects |
| GET | /medication/:id | Gets the specified medication object |
| POST | /medication/create | Creates a medication object |
| PUT | /medication/update/:id | Updates the specified medication object |
| DELETE | /medication/remove/:id | Removes the specified medication object |
| | | .... |

310

| | | |
|---|---|---|
| POST | /condition/create | Creates a condition for a user |
| GET | /condition/:action | Searches for condition information |
| | | .... |

312

| | | |
|---|---|---|
| GET | /hospital/summary/:provider_id | Get a user's clinical history. |
| | | .... |

314

| KEY | PARAMETER TYPE | DATA TYPE |
|---|---|---|
| provider_id | query | string |

320

```
{
  "success":true,
  "code":200,
  "data": {
    ...
  }
  ...
}
```

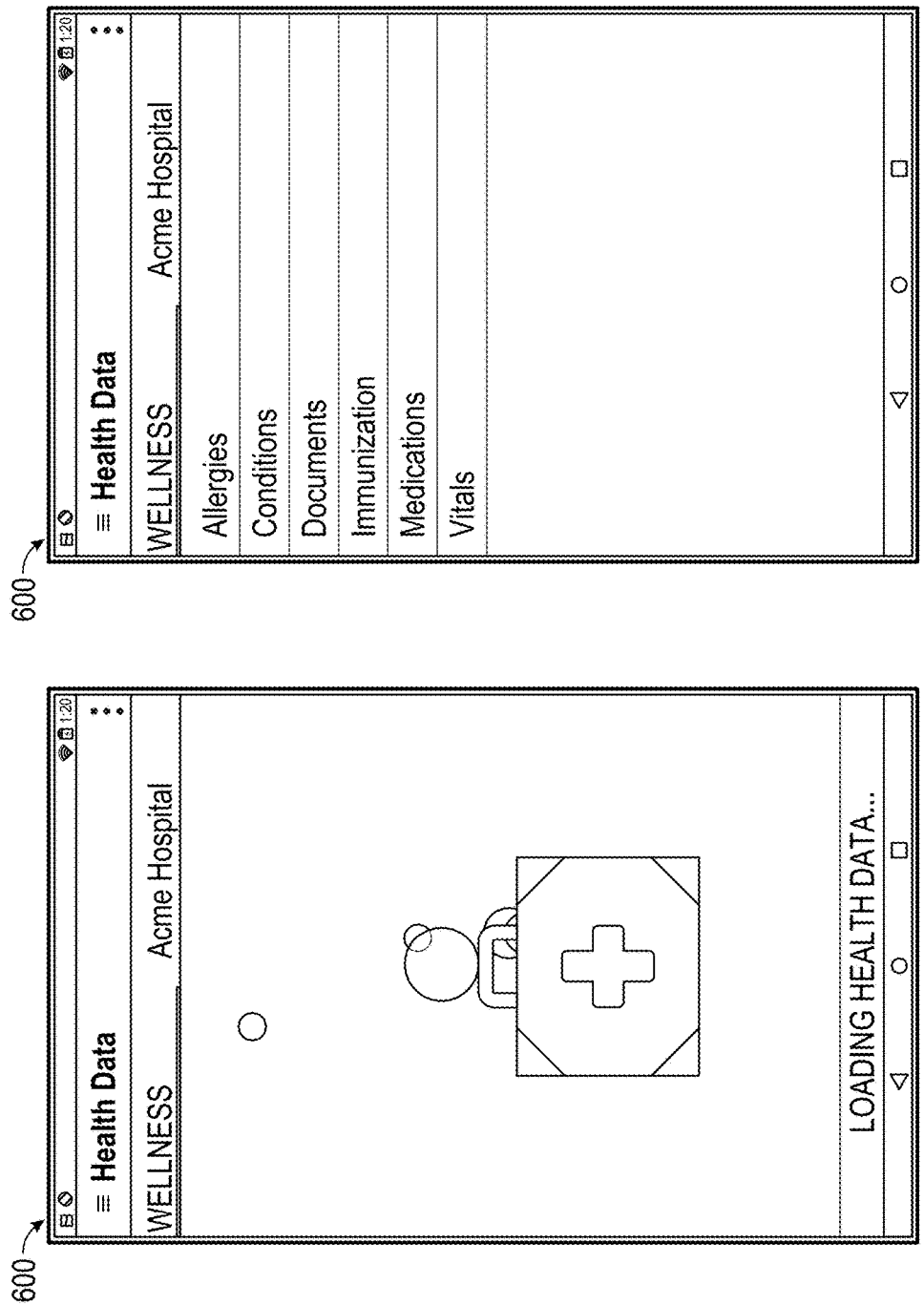

← Allergies

Avelox TABS
Abdominal pain

Codeine Derivatives

Penicillins
Rash

Bactrim TABS
Rash

Acetaminophen-Hydrocodone TABS

Cytomel TABS

LamISIL TABS

Morphine Sulfate TABS
Urgent Hives

Sulfa Drugs
Diarrhea,GI,Other

FIG. 6G

← Medications

| Active | Inactive |
|---|---|

⊘ AmLODIPine Besylate 5 MG Oral Tablet

⊘ Atorvastatin Calcium 10 MG Oral Tablet

⊘ Atorvastatin Calcium 40 MG Oral Tablet

⊘ Glimepiride 1 MG Oral Tablet

⊘ Januvia 50 MG Oral Tablet

⊘ LORazepam 0.5 MG Oral Tablet

< Back  Select Time

Meghan  MD

April  May  June

Sun Mon Tue Wed Thu Fri Sat
 1   2   3   4   5   6   7

Available appointment times

11:00am  *Office visit*
11:30am  *Office visit*
1:00pm  🗎 *Televisit*
3:00pm  🗎 *Televisit*

FIG. 10D

< Back  Visits

Upcoming

Meghan  MD  May 4, 2016

🗎 This appointment is a video call

```
{
"sendData":{
"\u000BMSH|^~\&|||ADM|TCM|||20160629113O|JADT^A03|700419|D|2.4||AL|NE|\
rEVN|A03|20160629113O|ENDEPER||REGISTA01^Regis|20160629112B|\rPID|1|TEXTVIG00026122134106|MU00034853^^^^MR^TCM^101-19-
7198^^^^SS^TCM^MU28680^^^^PI^TCM^TEXTVIG0002612^^^^HUB^TCM|MU28680|ZZI\TESTTCM^ONE^^^^^L|||19710101|M||AS|1971 ONE
RD^^LUBBOCK^TX^79401^^^^TX303||214-101-1971|806-791-3000|FRE|M|BAP|MA000002250011|101-19-7198||2|\
rNK1|1|NEXT^TCMVTHREE|AU^Aunt|1971 NEXT RD^^PONDER^TX^75701|682-101-1971|NOK|\rNK1|2|PERSON^TCMVTHREE|UN^Unknown|1971 PERSON
RD^^TYLER^TX^75701|469-101-1971|NOT|\rNK1|3|LOWES001||5022 W Loop 289^^Lubbock^Tx^79424||806-791-3000|EMP||||Lowes Home
Improvement-Lubbock|||||||||FT|\
rPV1||1|E|TCMED|EL||EEMMDHIE^TestHIE^Physician^^^^^^1234567893^^^XX|EEMMDHIE^TestHIE^Physician^^^^^^1234567893^^^XX|||||HOME|||E
R||XN|||||||HOME|||TCM||DEP||20160629O859|20160629112B|\rPV2|||CYCLE 4|||||||||||EL||||||||N|AM^Ambulance|\
rROL|1|AD|AT|EEMMDHIE^TestHIE^Physician^^^^^^1234567893^^^XX|\rOL|2|AD|RP|EEMMDHIE^TestHIE^Physician^^^^^^1234567893^^^XX|\
rROL|3|AD|PP|EEMMDHIE^TestHIE^Physician^^^^^^1234567893^^^XX|\rOBX|1|ST|1010.1^WEIGHT^CPT4||90.718475|kg||||||F|\
rOBX|2|ST|1010.3^HEIGHT^CPT4||165.1|cm||||||F|\rOBX|3|TX|AEACCO1^Is this Visit Accident Related?^ADM||N|||||F|\rOBX|4|CE|AEEFREL01^eForm
Signature Relationship:^ADM||SP^Self/Same as Patient|||||F|\rOBX|5|TX|AELANGINO1^Free Interpreter?^ADM||N|||||F|\rOBX|6|TX|AENOP^<< HIPAA
>> Notice of Privacy Practice Given:^ADM||N|||||F|\rOBX|7|TX|AEPATRIGHT^Patient Rights given/offered to patient?^ADM||N|||||F|\
rOBX|8|TX|AEREGCMP01^Patient Cleared by Registration?^ADM||Y|||||F|\rOBX|9|TX|AERESFA01^Restrict Fundraising Appeals?^ADM||N|||||F|\
rOBX|10|TX|AERESRCH01^Are You Here for a Research Study Visit?^ADM||N|||||F|\rOBX|11|CE|AESHLANG01^Primary/Preferred
Language:^ADM||FRE^French|||||F|\rOBX|12|TX|ATIMMTR01^IMMTRAC Consent Form:^ADM||20160629|||||F|\rOBX|13|TX|DSTOT01401^Pre-op
diagnosis^ADM||CYCLE 4|||||F|\rOBX|14|TX|DSTOT01501^Planned procedure/surgery^ADM||CYCLE 4A|||||F|\rOBX|15|CE|ETHN^Patient's
Ethnicity:^ADM||2^Not Hispanic/Not Latino|||||F|\rOBX|16|TX|LANGUAGE^Regulatory Preferred Language:^ADM||FRE|||||F|\
rOBX|17|CE|NIMINJEC02^IM Injection Site^ADM||4^Left Deltoid|||||F|\rOBX|18|TX|NO2SATPO^O2 Sat By Pulse Oximetry^ADM||99|||||F|\
rOBX|19|CE|NPNEUVAC03^Pneumococcal Vaccine Status^ADM||4^Never Immunized|||||F|\rOBX|20|TX|NRRRC^Respiratory Rate^ADM||19|||||F|\
rOBX|21|TX|NVACCEXD^Expiration Date^ADM||20170629|||||F|\rOBX|22|TX|NVACCLTN^Lot Number^ADM||NNNN|||||F|
\r\u001C\r"
],
"receiveData":[
"\u000BMSH|^~\&|||ADM|TCM||20160629113O||ACK|700419|D|2.4||AL|NE\rMSA|AA|700419\r\u001C\r"
],
"received_id":"74458332-6cd7-42e8-a5b9-1759b086a3b0",
"received_ts":"1467217826827"
}
```

FIG. 13A

```
{
  "_index":"patient_1",
  "_type":"patient",
  "_id":"7CFDA755E1B741226919B26C0EA350DF51111F9A",
  "_version":700423,
  "_score":1,
  "_source":{
    "patient_id":"7CFDA755E1B741226919B26C0EA350DF51111F9A",
    "adt_patient_id":"TEXTVIG0002612",
    "mrns":[
      "TCM|MU00031111"
    ],
    "first_name":"ONE",
    "last_name":"ZZIVTESTTCM",
    "ssn":"101-19-7198",
    "marital_status":{
      "lookup_key":"M",
      "lookup_val":"Married"
    },
    "date_of_birth":"1971-01-01T00:00:00Z",
    "date_of_birth_str":"01/01/1971",
    "sex":{
      "lookup_key":"M",
      "lookup_val":"Male"
    },
    "phone_number":"214-101-1971",
    "address":"1971 ONE RD",
    "city":"LUBBOCK",
    "state":"TX",
    "zip":"79401",
    "preferred_language":"French",
    "smoking_status":"Light Tobacco Smoker",
    "hie_opt_out":false,
    "other_obx":{

},
    "received_ts":"2016-06-29T16:30:26Z",
    "received_id":"7f451111-6cd7-42e8-a5b9-1759b086a3b0",
    "converted_ts":1469663111693,
    "converted_id":"0f74f801-6959-4677-8347-8b761111431c",
    "version":"700419",
    "data_source":"INT_LOCAL"
  }
}
```
⸻ 1304

FIG. 13B

```
 ┌─ 1306
 │ "request": {
 │ "body": "----boundary546.76470588235294125520.58823529411711---/n\r\nContent-Id: <payload@meditech.com>\r\nContent-Transfer-Encoding: binary\r\
 │ nCONTENT-TYPE: text/xml; charset=UTF-8; type=\"application/soap+xml\"\r\n\r\n<?xml-stylesheet type=\"text/xsl\" href=\"ccd.xsl\"?>\r\n<ClinicalDocument
 │ xmlns:sdtc=\"urn:hl7-org:sdtc\" xmlns:xsi=\"http://www.w3.org/2001/XMLSchema-instance\" xmlns=\"urn:hl7-org:v3\">
 │
 │ <associatedPerson>\r\n<name>\r\n<given>Physician</given>\r\n<family>TestHIE</family>\r\n</name>\r\n</associatedPerson>\r\n<associatedEntity>\r\
 │ n</participant>\r\n<participant typeCode=\"IND\">\r\n<templateId root=\"2.16.840.1.111111.3.88.11.32.3\"/>\r\n<associatedEntity classCode=\"NOK\">\r\
 │ n<code nullFlavor=\"UNK\"/>\r\n<addr>\r\n<streetAddressLine>1971 NEXT RD</streetAddressLine>\r\n<city>PONDER</city>\r\n<state>TX</state>\r\
 │ n<postalCode>75701</postalCode>\r\n</addr>
 │ ····
 │ <structuredBody>\r\n<component>\r\n<section>
 │ ····
 │ <title>Medications</title>\r\n<text>\r\n<content>Current Home Medications\r\n<br/>\r\n<table>\r\n<thead>\r\n<tr>\r\n<th>Medication</
 │ th>\r\n<th>Dose</th>\r\n<th>Units</th>\r\n<th>Route</th>\r\n<th>Directions</th>\r\n<th>Days/Qty</th>\r\n<th>Instructions</th>\r\n<th>Start
 │ Date</th>\r\n<th>Status</th>\r\n</tr>\r\n</thead>\r\n<tbody>\r\n<tr>\r\n<td ID=\"medication-1\">Aspirin</td>\r\n<td>81</td>\r\n<td>Mg</td>\r\n<td>
 │ <td>Oral</td>\r\n<td ID=\"rxsig-1\">Daily</td>\r\n<td>\r\n<td ID=\"rxinst-1\"/>\r\n<td>06/29/16</td>\r\n<td>Active</td>\r\n</tr>\r\
 │ n<tr>\r\n<td ID=\"medication-2\">Lisinopril</td>\r\n<td>5</td>\r\n<td>Mg</td>\r\n<td>Oral</td>\r\n<td ID=\"rxsig-2\">Daily</td>\r\n<td>30 Qty</
 │ td>\r\n<td ID=\"rxinst-2\"/>\r\n<td>06/29/16</td>\r\n<td>Active</td>\r\n</tr>\r\n</tbody>\r\n</table>\r\n</text>\r\n<entry>\r\
 │ n<substanceAdministration classCode=\"SBADM\" moodCode=\"INT\">\r\n<templateId root=\"2.16.840.1.113883.10.20.22.4.16\"/>\r\n<id root=\"70f156c2-
 │ 78d3-4473-ea8d-eb439d77376b\"/>\r\n<text>\r\n<reference value=\"#rxsig-1\"/>\r\n</text>\r\n<statusCode code=\"completed\"/>\r\n<effectiveTime
 │ xsi:type=\"IVL_TS\"/>\r\n<low value=\"20160629\"/>\r\n<high nullFlavor=\"UNK\"/>\r\n</effectiveTime>\r\n<repeatNumber value=\"1\"/>\r\n<routeCode
 │ code=\"C38288\" displayName=\"ORAL\" codeSystem=\"2.16.840.1.111111.3.26.1.1\" codeSystemName=\"National Cancer Institute (NCI) Thesaurus\"/>\r\
 │ n<doseQuantity value=\"81\" unit=\"mg\"/>\r\n<consumable>\r\n<manufacturedProduct classCode=\"MANU\">\r\n<templateId root=\
 │ "2.16.840.1.111111.10.20.22.4.23\"/>\r\n<manufacturedMaterial classCode=\"MMAT\">\r\n<code code=\"308416\" displayName=\"Aspirin 81 MG Delayed
 │ Release Oral Tablet\" codeSystem=\"2.16.840.1.113883.6.88\" codeSystemName=\"RxNorm\">\r\n<originalText>\r\n<reference value=\"#medication-1\"/>\r\
 │ n</originalText>\r\n</code>\r\n</manufacturedMaterial>\r\n</manufacturedProduct>\r\n</consumable>\r\n<performer typeCode=\"PRF\">\r\
 │ n<templateId root=\"2.16.840.1.113883.10.20.6.2.1\"/>
 │
 │ </section>\r\n</component>\r\n</structuredBody>\r\n</component>\r\n</ClinicalDocument>\r\n--
 │ boundary546.76470588235294125520.58823529411711---"
 │ },
 │ "requester_ts": 1467217877248,
 │ "requester_id": "1467217877248-9723cc3e-2e7d-4126-8be8-b72927900111",
 │ "application_name": "akoolaa"
 │ }
 └─
```

FIG. 13C

```
                        ┌─ 1308
┌─────────────────────/──────────────────────────────────────┐
│ {                                                          │
│  "_index": "medication_1",                                 │
│  "_type": "medication",                                    │
│  "_id": "35F2E57C0AC212517F9423A8E81B4F6C266DFE72",        │
│  "_score": 1.2724402,                                      │
│  "_source": {                                              │
│    "medication_id": "35F2E57C0AC212517F9423A8E81B4F6C266DFE72", │
│    "patient_id": "7CFDA755E1B741226919B26C0EA350DF58994F9A",    │
│    "name": "Aspirin",                                      │
│    "type": "Discharged",                                   │
│    "prescriber": "Testhie, Physician",                     │
│    "dose": "81",                                           │
│    "unit": "mg",                                           │
│    "form": "",                                             │
│    "route": "ORAL",                                        │
│    "directions": "Daily",                                  │
│    "days_qty": "30",                                       │
│    "instructions": "",                                     │
│    "start_date": "2016-06-29T00:00:00Z",                   │
│    "start_date_str": "06/29/2016",                         │
│    "status": "Active",                                     │
│    "source": "Acme Medical Center",                        │
│    "data_source": "INT_SC",                                │
│    "received_ts": "2016-06-29T16:31:17Z"                   │
│  }                                                         │
│ }                                                          │
└────────────────────────────────────────────────────────────┘
```

FIG. 13D

```
{
  "sendData": [
    "\u0000bMSH|^~\&|||TCM^1132150008^ISO|||201606290908||VXU^V04^VXU_V04|700331|D|2.5.1||||AL|NE|\
rPID|1||MU00034853^^^TEXAS.TEST5.67^MR^TCM^101-19-
7198^^^TEXAS.TEST5.67^SS^TCM^MU28680^^^TEXAS.TEST5.67^PI^TCM~TEXTVIG0002612^^^TEXAS.TEST5.67^XX^TCM^MA000022501 1^^^TEXAS.TEST5.67^A
N^TCM||ZZIVTESTTCM^ONE^^^^^L|||19710101|M||2028-9^Asian^HL70005|1971 ONE
RD^^LUBBOCK^TX^79401^USA^L||^PRN^PH^^1^214^1011971|^WPN^^^^806^7913000|||A|20160629|||M|BAP|MA00002250 11||||2|\
rPD1||||1234567893^TestHIE^Physician^^^^^^^^^NPI||||||N|20160629|||A|20160629|||N|20160629|||NEXT^TCMVTHREE^^^^^L|EXF|1971 NEXT
RD^^PONDER^TX^75701^USA^L|^PRN^PH^^^806^7913000|||NOK|\rNK1|2|PERSON^TCMVTHREE^^^^^L|UNK|1971 PERSON
RD^^TYLER^TX^75701^USA^L|^PRN^PH^^^469^1011971|NOT|\rNK1|3|LOWES001||5022 W Loop
289^^Lubbock^Tx^79424^USA^L||^^^^806^7913000|EMP|||||Lowes Home Improvement-Lubbock||||||||||||||FT|\
rPV1|1|R||EL|||1234567893^TestHIE^Physician^^^^^^^^^NPI||||||HOME|||||||||||||||||201606290859|\rPV2||||CYCLE
4||||||||EL||||||||N||AM^Ambulance|\rIN1|1|AET8200000|AETNA PPO|PO Box 981106^^EL PASO^TX^79998-
1107|^^^^888^6323862|||||LOWES001||||||||TLM C4 ONE|||FT||^^Lubbock|\rIN2|1|101-19-
7198||||||||^^^^1|||||||||||||||||||^PRN^PH^^^214^1011971|\
rORC|RE||CF00000066^TCM||||||EEMMDHIE^TestHIE^Physician^^^^^^Medical Cen||1234567893^TestHIE^Physician^^^^^^Medical Cen^L|\
rRXA|0|1|20160629 1106|201606291106|10^IPV^CVX|0.5|ML|00^New immunization
record^NIP001|REGISTA01^Regis^Tariq^^^^L|^^^1132150008^^^Covenant Medical Cen^^^3615 19TH
STREET^^Lubbock^TX^79410|||NNN|20170629|UNK^Berna Prod^MVX|||CP|A|\rRXR|IM|\rOBX|1|CE|64994-7^Patient Eligibility Category for Vaccine
Funding Program^LN|1|||||F|||20160629|||VXC40^Eligibility captured at the immunization level^CDCPHINVS|\u001c\r"
  ],
  "receiveData": [
    "\u0000bMSH|^~\&||||TCM^1132150008^ISO|201606290908||ACK|700331|D|2.5.1|||AL|NE|\rMSA|AA|700331|\u001c\r"
  ],
  "received_id": "463d12c2-9368-4813-be59-afd5ff0bc825",
  "received_ts": 1467216523589
}
```

FIG. 13E

```
{
 "_index": "immunization_1",
 "_type": "immunization",
 "_id": "7B9111E26CAB9E2FCF1D38A92C390B95779AC4BF",
 "_score": 0.82770085,
 "_source": {
  "immunization_id": "7B9111E26CAB9E2FCF1D38A92C390B95779AC4BF",
  "patient_id": "7CFDA111E1B741226919B26C0EA350DF58994F9A",
  "vaccine_name": {
   "lookup_key": "10",
   "lookup_val": "IPV"
  },
  "date": "2016-06-29T11:06:00Z",
  "date_str": "06/29/2016 11:06",
  "status": "A",
  "source": "Acme Medical Center",
  "vaccine_text": "IPV",
  "administered_amount": 0.5,
  "units": "ML",
  "name_of_coding_system": {
   "lookup_key": "CVX",
   "lookup_val": "CDC Vaccine Codes"
  },
  "data_source": "INT_TX",
  "received_ts": "2016-06-29T16:08:43Z"
 }
}
```

```
{
  "sendData": {
    "\u000bMSH|^~\&||LAB|SFM|||20160405125611-0800||ORU^R01|453959|D|2.3|\
rPID|1|SOCTVIG0002985^123578|FM00026751|FM222628|ZZITESTSFM^HARTONE||19800105|F||WH|222 LANE^^SPOKANE^WA^99037||999-888-1212||ENG|S|LUT|FV0000138355|999-88-1212|\rPV1|1|O|SFMLAB|EL|}
^Physician^SoCal^^^^^^1234567893^^^XX||||||||||||SFM||REG|||20160121T1434|\
rROL|1|AD|AT|SUMMD^Physician^SoCal^^^^^^1234567893^^^XX|\rROL|2|AD|PP|SUMMD^Physician^SoCal^^^^^^1234567893^^^XX|\rIN1|1|SP|Self
Pay|||||SP|ABBOTO01|||||ZZITESTSFM^HARTONE|SP|||||||||||||F|^Full-Time Employed||^^Irvine|\rORC|RE|13051^LAB|13051|\
rOBR|1|13051^LAB|13051^LAB^00010100|LIPIDR^Panel, Lipid - Direct LDL
Rflx^L^^^LN|R||20160405123Q||DV|||VALIDATION|20160405123q||SUMMD^Physician^SoCal^^^^^^1234567893^^^XX||00010100||0405:C00022R||||LAB|CO
MPLETED||^^^^^R|\rOBX|1|ST|CHOL^Cholesterol Level^L^^^LN|1|200|mg/dL|<200|H||A^S|F|||20160405124|SFML^SJH - SJF Lab  (main)^L|\rNTE|1||Reference
ranges given reflect the recommendations of the|\rNTE|2||National Cholesterol Education Program (NCEP,2001);|\rNTE|3||    <200    Desirable|\rNTE|4||   200-
239    Borderline High|\rNTE|5||    >=240     High|\rOBX|2|ST|TRIGR^Triglyceride^L^^^LN|1|100|mg/dL|<150|N||A^S|F|||20160405124|SFML^SJH - SJF Lab
(main)^L|\rNTE|6||Reference ranges given reflect the recommendations|\rNTE|7||of the American Cholesterol Education Program.|\rNTE|8||Fasting blood
triglyceride levels in adults:|\rNTE|9||    <150    Optimal|\rNTE|10||150-199    Borderline-high|\rNTE|11||200-499    High|\rNTE|12||   >500    Very High|\
rOBX|3|ST|HDL^Cholesterol, HDL^L^^^LN|1|40|L||A^S|F|||20160405124|SFML^SJH - SJF Lab  (main)^L|\rNTE|13||Reference ranges given reflect the
recommendation of the|\rNTE|14||National Cholesterol Education Program (NCEP,2001);|\rNTE|15||    <40  Low     >=60 High|\rOBX|4|ST|TNHDL^Non-HDL
Cholesterol Calculated^L^^^LN|1|160|mg/dL|<130|H||A^S|F|||20160405124|SFML^SJH - SJF Lab  (main)^L|\rOBX|5|ST|VLDL^VLDL Cholesterol^L^^^LN|1|20|mg/dL|<30|N||A^S|F|||20160405124|SFML^SJH - SJF Lab  (main)^L|\rNTE|16||Please note new formula(TC-HDL)as of July
2, 2012.|\rOBX|6|ST|CRF^Coronary Heart Dis Risk Ratio^L^^^LN|1|5.00||3.27-4.44|H||A^S|F|||20160405124|SFML^SJH - SJF Lab  (main)^L|\rNTE|17|| MEN         WOMEN        RELATIVE RISK|\
rNTE|18||   3.43      3.27       Below average|\rOBR|2|13051^LAB|13051^LAB^00010100|GTT2.T^Glucose Tolerance, 2
Hr^L^^^LN|R||20160405123Q||DV|||VALIDATION|20160405123q||SUMMD^Physician^SoCal^^^^^^1234567893^^^XX||00010100||0405:C00022R||||LAB|COM
PLETED||^^^^^R|\rOBX|1|ST|GTT2.T^Glucose Tolerance, 2 Hr^L^^^LN|1||MG/DL||H||A^S|F|||20160405125|SFML^SJH - SJF Lab  (main)^L|\rNTE|22||FASTCOLA
Query Trigger    Rng:|\rNTE|23||Col: 04/05/16 1230|\rNTE|24||GLUCOLA  100 grams       Rng:|\rNTE|25||Col: 04/05/16 1230|\rNTE|26||FAST (POC) 90
Rng:60-110 mg/dL|\rNTE|27||Col: 04/05/16 1230|\rNTE|28||FASTING  NP          Rng:60-110 mg/dL|\rNTE|29||Col: 04/05/16 1230|\rNTE|30||1HR GLU
130    Rng:120-170 mg/dL|\rNTE|31||Col: 04/05/16 1330|\rNTE|32||2HR GLU 200 H         Rng:70-120 mg/dL|\rNTE|33||Col: 04/05/16 1430|\
rNTE|34||Glucola dose: 100|\rNTE|35||Fasting POC Glucose: 90|\rNTE|36||Do you have a Fasting POC glucose or Glucola dose value? Y|\u001c|r"
},
"receiveData": {
"\u000bMSH|^~\&|||LAB|SFM|20160405125611-0800||ACK|453959|D|2.3\rMSA|AA|453959\r\u001c\r"
},
"received_id": "6769ce2a-ccc9-4fbe-8a60-dc74e93f1236",
"received_ts": 1459886197436
}
```

1316A
```
{
  _index: "lab_1",
  _type: "lab",
  _id: "20A4E7C44D0EFBEA6416E69FD63F5F8A04FCA111",
  _score: 0.4170827,
  _source: {
    lab_id: "20A4E7C44D0EFBEA6416E69FD63F5F8A04FCA111",
    patient_id: "E59C7EDC8B9773BF9532F19C680B2EB1941115ED",
    encounter_id: "2D6E1F9FC87D0E208C69D63F884F39C7811117D5",
    date_time_collected_str: "2016-04-05T12:30:00Z",
    date_time_collected: "04/05/2016 12:30",
    date_time_received_str: "2016-04-05T12:39:00Z",
    date_time_received: "04/05/2016 12:39",
    date_time_of_results_str: "2016-04-05T14:30:00Z",
    date_time_of_results: "04/05/2016 14:30",
    source: "Acme Health",
    results: {
      1HR GLU Flag: "",
      Glucose Tolerance, 2 Hr Performed At: "SFML",
      FAST (POC) Date: "2016-04-05T12:30:00.000Z",
      GLUCOLA Performed At City: "Fullerton",
      1HR GLU Unit: "mg/dL",
      FASTCOLA Query Trigger Flag: "",
      FASTCOLA Query Trigger: "",
      FAST (POC) Performed At: "SFML",
      FAST (POC) Position: "4",
      2HR GLU: "200",
      1HR GLU Performed At Address: "1 Acme Dr.",
      1HR GLU Date: "2016-04-05T13:30:00.000Z",
      GLUCOLA Performed At Address: "101 Acme Dr.",
      2HR GLU Performed At Address: "101 Acme Dr.",
      FASTCOLA Query Trigger Performed At State: "CA",
```

1316B
```
      FAST (POC) Performed At Address: "1 Acme Dr.",
      Glucose Tolerance, 2 Hr Performed At Zip: "92835",
      2HR GLU Performed At State: "CA",
      FASTCOLA Query Trigger Performed At: "SFML",
      FAST (POC) Range: "60-110",
      Glucose Tolerance, 2 Hr Performed At State: "CA",
      Glucose Tolerance, 2 Hr: null,
      2HR GLU Range: "70-120",
      FASTING NP Performed At City: "Fullerton",
      FAST (POC) Performed At Zip: "92835",
      1HR GLU Comment: "",
      FASTCOLA Query Trigger Performed At City: "Fullerton",
      1HR GLU Range: "120-170",
      GLUCOLA Date: "2016-04-05T12:30:00.000Z",
      FASTING NP Unit: "mg/dL",
      2HR GLU Unit: "mg/dL",
      GLUCOLA Unit: "grams",
      Glucose Tolerance, 2 Hr Performed At Address: "1 Acme Dr.",
      FASTCOLA Query Trigger Date: "2016-04-05T12:30:00.000Z",
      2HR GLU Performed At: "SFML",
      FASTING NP Range: "60-110",
      1HR GLU Performed At: "SFML",
      GLUCOLA Flag: "",
      FAST (POC) Performed At State: "CA",
      FAST (POC) Comment: "",
      FASTING NP Performed At: "SFML",
      1HR GLU Performed At Zip: "92835",
      GLUCOLA Performed At: "SFML",
      FAST (POC) Performed At City: "Fullerton",
      FAST (POC): "90",
      FASTCOLA Query Trigger Performed At Zip: "92835",
      Glucose Tolerance, 2 Hr Flag: "H",
```

FIG. 13I

1316C
```
2HR GLU Flag: "H",
FASTING NP Flag: "",
FASTING NP: "",
FASTING NP Comment: "",
GLUCOLA Range: "",
2HR GLU Comment: "",
1HR GLU Performed At City: "Fullerton",
1HR GLU Position: "6",
Glucose Tolerance, 2 Hr Date: "2016-04-05T12:56:00.000Z",
2HR GLU Performed At City: "Fullerton",
GLUCOLA Performed At Zip: "92835",
FAST (POC) Unit: "mg/dL",
2HR GLU Position: "7",
FASTING NP Position: "5",
1HR GLU: "130",
FASTING NP Performed At Address: "1 Acme Dr.",
FASTING NP Performed At Zip: "92835",
FASTCOLA Query Trigger Comment: "",
FASTING NP Performed At State: "CA",
Glucose Tolerance, 2 Hr Position: "1",
FASTCOLA Query Trigger Position: "2",
2HR GLU Date: "2016-04-05T14:30:00.000Z",
Glucose Tolerance, 2 Hr Range: "",
GLUCOLA Performed At State: "CA",
GLUCOLA: "100",
GLUCOLA Position: "3",
Glucose Tolerance, 2 Hr Comment: "",
FASTCOLA Query Trigger Range: "",
GLUCOLA Comment: "",
Glucose Tolerance, 2 Hr Unit: "MG/DL",
FASTCOLA Query Trigger Performed At Address: "1 Acme Dr.",
FASTCOLA Query Trigger Unit: "",
```

1316D
```
1HR GLU Performed At State: "CA",
2HR GLU Performed At Zip: "92835",
FAST (POC) Flag: "",
FASTING NP Date: "2016-04-05T12:30:00.000Z",
Glucose Tolerance, 2 Hr Performed At City: "Fullerton"
},
queries: "Glucola dose: 100 Fasting POC Glucose: 90 Do you have a Fasting POC glucose or Glucola dose value? Y",
status: "FINAL",
type: "Glucose Tolerance, 2 Hr",
performed_at: "",
specimen_number: "0405:C00022R",
mrn: "SFM|FM00026751",
encounter_number: "FV00001383555",
admit_date: "2016-01-21T14:34:00Z",
admit_date_str: "01/21/2016 14:34",
encounter_type: "O",
attending_doctor: {
first_name: "SoCal",
npi: "1234567893",
last_name: "Physician",
id: "SUMMD"
},
ordering_provider: {
first_name: "SoCal",
npi: "1234567893",
last_name: "Physician",
id: "SUMMD"
},
reason_for_visit: "",
data_source: "INT_SC",
version: "453959",
received_ts: "2016-04-05T19:56:37Z"
}
```

```
"sendData": [
"\u000bMSH|^~\&|||ITS|TCM^TCM|||20160629091919|ORU^R01|700401|D|2.3|||AL|NE|\
rPID|1|TEXTV|G0002612^134106|MU28680|ZZIVTESTTCM^ONE^^^^^L||19710101|M||AS|1971 ONE RD^^LUBBOCK^TX^79401||214-101-1971|806-791-3000||M|BAP|MA00002225011|101-19-7198|\
rPV1|1|E|TCMED|EL||||EEMMDHIE^TestHIE^Physician^^^^^^^^1234567893^^^XX|EEMMDHIE^TestHIE^Physician^^^^^^^^1234567893^^^XX||||HOME|||E R||XN|||||||||||||||TCM|||REG||20160629|0859|\rROL|1|AD|AT|EEMMDHIE^TestHIE^Physician^^^^^^^^1234567893^^^XX|\
rROL|2|AD|RP|EEMMDHIE^TestHIE^Physician^^^^^^^^1234567893^^^XX|\rROL|3|AD|PP|EEMMDHIE^TestHIE^Physician^^^^^^^^1234567893^^^XX|\
rIN1|1|AET820000||Aetna PPO|PO Box 981106^^EL PASO^TX^79998-1107||888-632-3862|||PPO|LOWES001|||||ZZIVTESTTCM^ONE|SP|19710101|1971 ONE RD^^LUBBOCK^TX^79401|||||||||||||||||TLM C4 ONE|||||F^Full-Time Employed|M|^^Lubbock||vORC|RE|1872.001TCM|CVS20160629-0001||||||EEMMDHIE^TestHIE^Physician^^^^^^^^1234567893^^^XX|||No|\vOBR|1|1872.001TCM|CVS20160629-0001|EKG^EKG^EKG/ECG|R|20160629090|20160629090|20160629091116|||EEMMDHIE^TestHIE^Physician^^^^^^^^1234567893^^^XX||||EEMMDHIE^TestHIE^Physician^^^^^^^^1234567893^^^XX||||REGISTA01^Regis^Tariq|\vOBX|1|TX||| 1234567893||EKG20160629-0001||CVS|EKG||||S||||EEMMDHIE^TestHIE^Physician^^^^^^^^1234567893^^^XX||||REGISTA01^Regis^Tariq|\vOBX|1|TX||| Covenant Medical Center |\vOBX|2|TX||| 3615 19th Street |\vOBX|3|TX||| Lubbock, TX 79410 |\vOBX|4|TX|||  |\vOBX|5|TX|||
Electrocardiology Report |\vOBX|6|TX||| |\vOBX|7|TX||| |\vOBX|8|TX|||Patient Name: ZZIVTESTTCM,ONE DOB: 01/01/1971 |\vOBX|9|TX|||Account #: MA00002225011 Age/Sex: 45/M |\vOBX|10|TX|||Unit #: MU00034853 Location: TCMED |\vOBX|11|TX||| |\vOBX|12|TX|||Ordering Dr: TestHIE,Physician |\vOBX|13|TX|||Exam Performed: EKG/ ECG |\vOBX|14|TX|||Service Date: 06/29/16 |\vOBX|15|TX|||Req #: 0629-0001 |\vOBX|16|TX||| Accession #: 1872.001TCM |\vOBX|17|TX|||Dictating Dr: Physician TestHIE MD |\vOBX|18|TX|||Primary Dr: TestHIE,Physician |\vOBX|19|TX||| |\vOBX|20|TX||| |\
rOBX|21|TX|||C |\vOBX|22|TX|||Y |\vOBX|23|TX|||L |\vOBX|24|TX|||E |\vOBX|25|TX|||E |\vOBX|26|TX|||4 EKG |\vOBX|27|TX|||4 EKG |\vOBX|28|TX||| |\
rOBX|29|TX||| |\vOBX|30|TX||| |\vOBX|31|TX|||Authenticated By: |\vOBX|32|TX||| 06/29/16 1117 |\
rOBX|33|TX|||_____ |\vOBX|34|TX|||Physician TestHIE MD |\vOBX|35|TX||| |\vOBX|36|TX||| |\
rOBX|38|TX||| |\vOBX|39|TX||| |Report #: 0629-0001 |\vOBX|40|TX|||Dictated date/time: 06/29/16 0900 |\vOBX|41|TX|||Transcription date/time: 06/29/16 1116 |\vOBX|42|TX|||Transcriptionist: REGISTA01 |\vOBX|43|TX||| |\vOBX|44|TX|||CC: |\vOBX|45|ED|||^text^html^Base64^PHNOcm9uZz48c3Bh
MHB0OyBjb2xvcjogMDAwMDAwOyI+PGJyPgONCg==|\rZES|1|EEMMDHIE|\vZEO|1|1872.001^EKG/ ECG|\r\u001c\r"
],
"receiveData": [
"\u000bMSH|^~\&||||ITS|TCM^TCM|20160629091919||ACK|700401|D|2.3|||AL|NE|rMSA|AA|700401|\r\u001c\r"
],
"received_id": "967c6530-e174-4b0a-a685-1ca0b06d5e62",
"received_ts": 1467217171876
}
```

FIG. 13J

```
{
_index: "imaging_1",
_type: "imaging",
_id: "225E30062F538C0D637F7158D25F347A1F111FBD",
_score: 0.15947711,
_source: {
imaging_id: "225E30062F538C0D637F7158D25F347A1F111FBD",
patient_id: "7CFDA755E1B741116919B26C0EA350DF58994F9A",
encounter_id: "2E0593BA27E6B92AB7C6DE6922932FD2111170B9",
date_time_collected: "2016-06-29T09:00:00Z",
date_time_collected_str: "06/29/2016 09:00",
date_time_dictated: "2016-06-29T09:00:00Z",
date_time_dictated_str: "06/29/2016 09:00",
source: "Acme Medical Center",
results: "<strong><span style="font-family: Verdana; font-size: 10pt; color: 000000;">
....
<span style="font-family: Verdana; font-size: 10pt; color: 000000;"><br>",
status: "S",
type: "EKG/ ECG",
mrn: "TCM|MU00034853",
encounter_number: "MA0000225011",
admit_date: "2016-06-29T08:59:00Z",
admit_date_str: "06/29/2016 08:59",
encounter_type: "E",
attending_doctor: {
first_name: "Physician",
npi: "1234567893",
last_name: "TestHIE",
id: "EEMMDHIE"
},
ordering_provider: {
first_name: "Physician",
npi: "CN",
last_name: "TestHIE",
id: "EEMMDHIE"
},
reason_for_visit: "",
document_name: "Electrocardiology Report",
accession_number: "1872.001TCM",
data_source: "INT_TX",
version: "700401",
received_ts: "2016-06-29T16:19:31Z"
}
}
```

FIG. 13K

```
{
  "sendData": {
    "\u000bMSH|^~\\&|||TCM|||20160629113O||ADT^A08|700420|D|2.3.1||||AL|NE|\rEVN|A08|20160629113O|||REGISTA01^Regis^Tariq|20160629112B|\
rPID|1|TEXTV!G0026l2^l34106|MU00034853^^^&TCM&ISO^PI^TCM|MU28680|ZZ|VTESTTCM^ONE^^^^^L|||19710101|M|AS|1971 ONE
RD^^LUBBOCK^TX^79401^^^^TX303||214-101-1971|806-791-3000||M|BAP|MA00002250l1|101-19-7198|\
rPV1|1|E|TCMED|EL|||EEMMDHIE^TestHIE^Physician^^^^^^^^XX||||HOME||||ER||XN|||||||||||
HOME|||TCM||DEP|||20160629O859|20160629112B|\rZDS|1|Smoking Status|\rOBX|1|CE|ZSMOKEST^Smoking Status|2^Light Tobacco
Smoker||||||20160629l109|\rZDS|2|Vital Signs|\rOBX|1|TX|Temperature|1|99 degrees F (97.6 - 100.4)|||||06/29/2016 11:10am|\
rOBX|2|TX|Patient Temperature|1|37.23 degrees C (36.4 - 38.0)|||||06/29/2016 11:10am|\rOBX|3|TX|Pulse Rate|2|99 bpm (60 - 100)|||||06/29/
2016 11:10am|\rOBX|4|TX|Respiratory Rate|3|19 breaths per min (12 - 20)|||||06/29/2016 11:10am|\rOBX|5|TX|Bedside Pulse Oximetry|3|99 % (92 -
100)|||||06/29/2016 11:10am|\rOBX|6|TX|Blood Pressure|4|99/66 mmHg|||||06/29/2016 11:10am|\rOBX|7|TX|Height|5|5 ft 5 in |||||06/
29/2016 11:05am|\rOBX|8|TX|Weight|6|200 lb |||||06/29/2016 11:05am|\rOBX|9|TX|Body Mass Index|7|33.35 |||||06/29/2016 11:05am|\
rZDS|3|Care Plan Instructions|\rZDS|4|Care Plan Goals|\rZDS|5|Functional/Cognitive Status|\rZDS|6|Referrals|\rZDS|7|Chief Complaint/Reason For Visit|\
rZDS|8|Advance Directives|\rOBX|1|CE|ZADVHED|^Does Patient Have Advance Healthcare Directive||N^No|||||||20160629O852|\r\u001c\r"
  },
  "receiveData": {
    "\u000bMSH|^~\\&|||TCM|20160629113O||ACK|700420|D|2.3.1||||AL|NE|\rMSA|AA|700420|\r\u001c\r"
  },
  "received_id": "6c9c91cd-b372-456d-813a-51f796785418",
  "received_ts": 1467217850815
}
```

```
                                      ┌── 1324
                                     /
┌─────────────────────────────────────────────────────────────┐
│ {                                                           │
│   "_index": "vitals_1",                                     │
│   "_type": "vitals",                                        │
│   "_id": "70A6C90383C6BABF427174B3ACBC9F6E61111C6F",        │
│   "_score": 1.0649408,                                      │
│   "_source": {                                              │
│     "vitals_id": "70A6C90383C6BABF427174B3ACBC9F6E61111C6F",│
│     "patient_id": "7CFDA755E1B741226919B26C0EA350DF11114F9A",│
│     "encounter_id": "2E0593BA27E6B92AB7C6DE6911112FD2196970B9",│
│     "date_time": "2016-06-29T11:10:00Z",                    │
│     "date_time_str": "06/29/2016 11:10am",                  │
│     "temperature": "99°F",                                  │
│     "blood_pressure": "99/66 ",                             │
│     "pulse": "99 bpm ",                                     │
│     "respiratory_rate": "19 bpm",                           │
│     "o_2_saturation": "99 % ",                              │
│     "source": "Acme Medical Center",                        │
│     "data_source": "INT_TX",                                │
│     "received_ts": "2016-06-29T16:30:50Z"                   │
│   }                                                         │
│ }                                                           │
└─────────────────────────────────────────────────────────────┘
```

Please enter your PIN code

| 1 | 2 | 3 |
| 4 | 5 | 6 |
| 7 | 8 | 9 |
|   | 0 | ⌫ |

FIG. 14B

Today, February 23, 2016

| 8:00 AM  | Malone    | Adams, MD   |
| 8:30 AM  | Banks     | Adams, MD   |
| 9:00 AM  | Fernandez | Gibbons, MD |
| 9:30 AM  | Williams  | Adams, MD   |
| 10:00 AM | Casey     | Gibbons, MD |
| 10:30 AM | Drake     | Gibbons, MD |
| 11:00 AM | Hernandez | Adams, MD   |
| 11:30 AM | Watkins   | Gibbons, MD |
| 12:00 PM | Saunders  | Gibbons, MD |
| 12:30 PM | Moore     | Adams, MD   |
| 13:00 PM | Buchanan  | Gibbons, MD |
| 13:30 PM | Wright    | Adams, MD   |
| 14:00 PM | Ball      | Adams, MD   |
| 14:00 PM | Smith     | Adams, MD   |

1400

Patient Schedule
○ Demographics ○ Insurance ○ Payments

Please fill out your demographics form
Sharing your demographics details now will ensure your doctors have the latest information about you!

Start

Cancel   Registration Form   Skip

Hello Josh, what is your email address?

art@mail.com

Skip   Next

FIG. 14D

Registration Form

What is your phone number?
At least one number is required.

Mobile* +1(555) 555-5555
Home +1(555) 555-5555
Work +1(555) 555-5555
Appointment Reminders   Call or Text

[ Next ]

Registration Form

What is your home address?

Street Address   5 S Empire
Zip   90210
City   Irvine
State   CA

[ Next ]

Authorization Form

Eligibility Guarantee

I hearby certify that I am eligible with the health insurance company under the subscriber indicated on my registration sheet. I also certify that I have chose _____ Medical Group to provide healthcare services. I understand that if the above is not true or I am not eligible under the terms of my Medical and Hospital Subscriber Agreement, I am liable for any and all charges for services rendered. Also, if the above is not true, I agree to pay in full for all services rendered within thirty days of receiving a bill.

Please sign here

[Clear Signature] [Done Signing]

FIG. 14G

Registration Form

What is your ethnicity?

Ethnicity       Non-Hispanic or Latino

Please note: As a results of new government regulations, all patients will be asked to identify their race and ethnicity as well as preferred language. This information is important to your doctor as some medical conditions may be common amongst certain racial or ethnic backgrounds. St. Joseph Heritage Healthcare is dedicated to improving the overall quality of health care and we thank you for providing the information requested below.

[Next]

FIG. 14L

Back

Payment

Amount due today is $40.00
Please enter your payment details below to pay for this visit.

Card Details

| | |
|---|---|
| Name on Card | Casey |
| Card Number | **** **** **** 4891 |
| Expiration Date | 09/2018 |
| Security Code | 101 |

Billing Address

| | |
|---|---|
| Street Address | 5 S Empire |
| Zip | 90210 |

[ Pay ]

FIG. 14M

Patient Schedule

⊙ Demographics  ⊙ Insurance  ⊙ Payments

You have been successfully checked in!

Please return the ipad to the clerk and have a seat. The doctor will be with you shortly.

SYSTEMS AND METHODS FOR BI-DIRECTIONAL DATABASE APPLICATION PROGRAMMING INTERFACE, EXTRACT TRANSFORM AND LOAD SYSTEM, AND USER COMPUTING DEVICE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

This application claims benefit of U.S. Provisional Patent Application Ser. No. 62/368,981 entitled "Systems And Methods For A Dynamic Bi-Directional Database Application Programming Interface And A Dynamic Extract Transform And Load System" filed Jul. 29, 2016, U.S. Provisional Patent Application Ser. No. 62/380,965 entitled "Systems And Methods For Bi-Directional Database Application Programming Interface, Extract Transform And Load System, And User Computing Device" filed Aug. 29, 2016, and U.S. Provisional Patent Application Ser. No. 62/433,708 entitled "HEALTH USER INTERFACE APPLICATION" filed Dec. 13, 2016, which are hereby incorporated by reference in their entireties.

BACKGROUND

In the area of computer-based platforms, data may be normalized, stored in a database, and queried.

BRIEF DESCRIPTION OF THE DRAWINGS

The following drawings and the associated descriptions are provided to illustrate embodiments of the present disclosure and do not limit the scope of the claims.

FIG. 3 depicts example communication interface routines, data types, and/or output.

FIGS. 6A-6I illustrate example graphical user interfaces of a user computing device.

FIGS. 9A-9C illustrate additional example graphical user interfaces of a user computing device.

FIGS. 10A-10D illustrate additional example graphical user interfaces of a user computing device.

FIGS. 13A-13M depict example input and/or output of the bi-directional communication system, dynamic extract, transform, and load system, and/or data exchange service.

FIGS. 14A-14M illustrate additional example graphical user interfaces of a user computing device.

DETAILED DESCRIPTION

Figure 1:
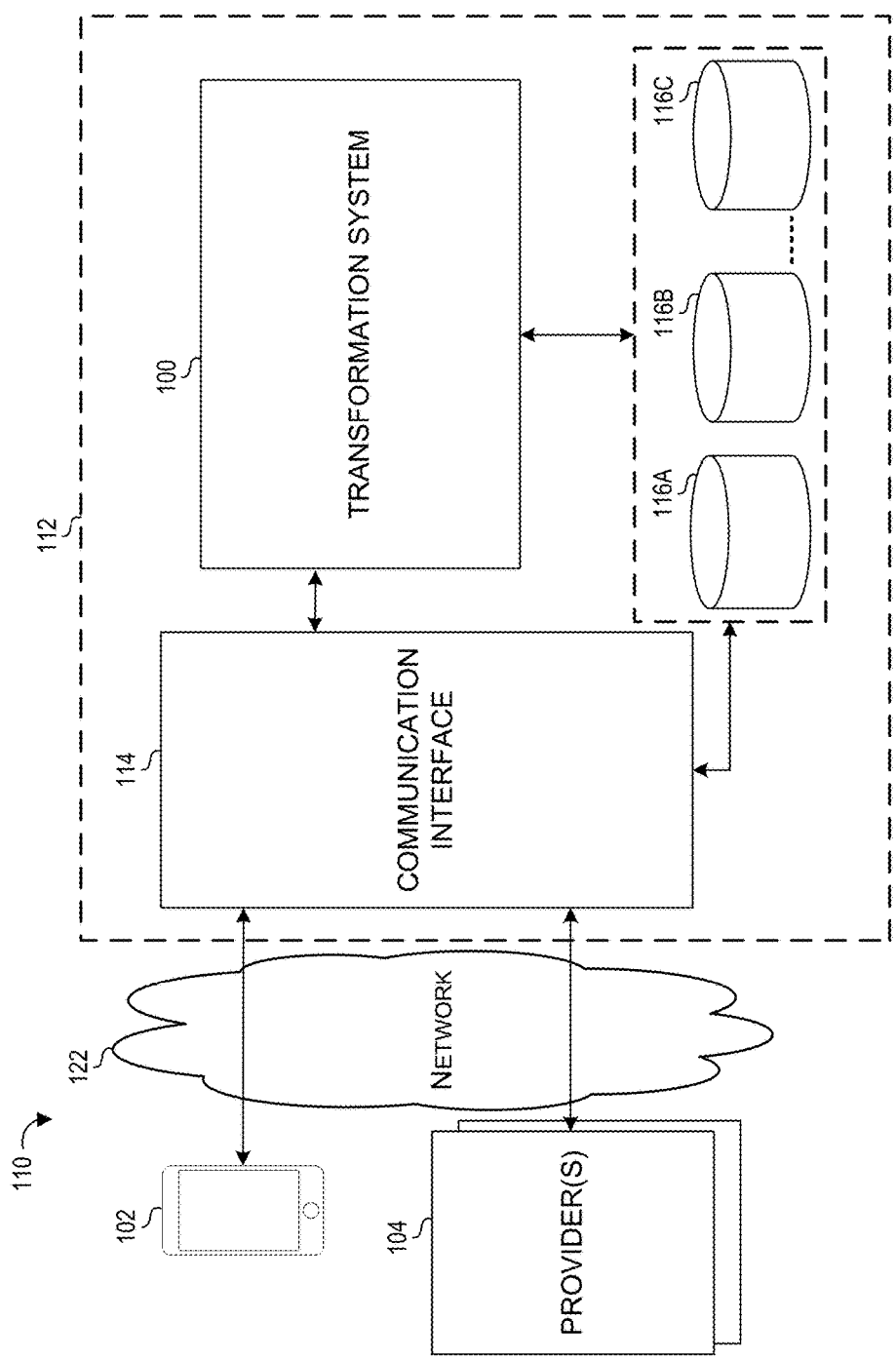
FIG. 1 is a block diagram illustrating an example bi-directional communication system, dynamic extract, transform, and load system, and/or data exchange service.

Various aspects of the disclosure will now be described with regard to certain examples and embodiments. They are intended to illustrate but not to limit the disclosure. Nothing in this disclosure is intended to imply that any particular feature or characteristic of the disclosed embodiments is essential.

It may be beneficial for disparate computing systems operating on various platforms to communicate and/or exchange data with one another. One approach is to normalize and store data from multiple disparate electronic record systems in a standardized format in a database. However, data centralization and/or normalization may result in inefficiencies and/or inaccuracies in the data. Moreover, problems with processing, storing, and providing data arise when data comes from different sources and is in different formats. For example, patient's medical data may be maintained by different providers in different formats.

Disclosed herein are embodiments of systems and methods that may be used to advantageously exchange data between disparate computing systems in an efficient and accurate manner. The disparate computing systems may include different electronic record systems, different information systems, and/or various user computing devices. For example, data may be collected from disparate data sources and transformed and/or integrated according to one or more predefined formats. The data may be transmitted via bi-directional, secure, and/or customizable communication interfaces. The exchange and/or storage of the data may comply with one or more regulations and/or laws. The data may be stored in its original form from respective data sources and transformed in stream and/or batch processes into the one or more predefined formats. Individual transformations may be stored and/or recorded. For example, the storage and/or recordation of transformations may correspond to an audit log. Individual providers and/or consumers of data may specify how the data should be transformed, such as de-identified, who can access the data, and/or for what period of time it may be accessible. The data from multiple data sources may be integrated and/or grouped according to one or more identification processes. The transformed and/or integrated data can be provided to one or more computing devices via the communication interfaces. The systems and methods described herein may improve the accuracy, security, and efficiency of data processing and/or computing systems. For example, the systems and techniques described herein may improve the functioning of the computer and/or computing systems, such as increased flexibility in data processing, faster search and/or transformation times, and/or improved data security.

Relational databases typically follow a number of rules and guidelines for organizing data items, such as data normalization. A relational database specifies that each data item be uniquely classified as a particular instance of a relation. Each set of relations is stored in a distinct table. Each row in the table represents a particular data collection, and each column represents an attribute that is shared over all data items in that table. In information exchanges, data from multiple data sources are sometimes stored in normalized format in relational databases. Accordingly, data from two different systems, which may originate in different formats, are transformed into a single data format in the relational database. Accordingly, inaccuracies may arise in the data normalization. For example, in a health information exchange context, lab results from a data provider may include five decimal places of precision and lab results from a different data provider may include four decimal places of precision. Continuing with the example, the normalized database of the health information exchange may only store three decimal places of precision, and, therefore, storing the lab results from the data providers results in loss of precision. Thus, a consumer of the data that requests lab data for four or five decimal places cannot achieve such precision from the health information exchange. Moreover, databases also typically follow the create, read, update, and delete (CRUD) model. Accordingly, updates and/or deletions to a row in the database permanently affect downstream consumers of such data. The systems and techniques described herein may allow for more flexible and/or reliable data exchanges.

An example implementation of the relational database model is where providers require other networks to place their data into a central repository. This data is often manipulated in an attempt to normalize all of the data to an even baseline before ever sending the data to the end repository. Depending on the system, different workflows are utilized by the provider to move data; if batches are incorrectly processed on the data, duplicate records are made, or even entire batch processes have to be rerun. When data is shared across networks, entire record sets are shared rather than individual data points. The medium of exchange is only set by running a VPN tunnel and then often sending the data raw, above layer 3 of the Open Systems Interconnection (OSI) model. Once data has been moved from one provider to another, audit logs of whom has touched or viewed the data (if they exist at all) often lives only on the originating systems, which makes building compliance reports a taskly process.

The systems and methods described herein may be intrinsically tied to network and/or computer technology because such solutions may be related to communication over computer networks, Application Programming Interfaces, data processing, and/or computer data security. For example, the data communication techniques and solutions described herein may be intrinsically tied to computer networks and/or one or more network protocols, such as HTTP. The processes for efficiently transforming data according to multiple data formats in a batch and/or stream manner for improved query times also may be intrinsically tied to database technology.

The systems and methods described herein may improve computer-related technology. In some embodiments, a data exchange service and/or transformation system may improve over relational databases and/or address the deficiencies of data normalization. The data exchange service and/or transformation system may store the original data in its original format as received from one of multiple disparate data sources. The data schema and/or data stores of the data exchange service may not follow the CRUD pattern. The underlying data store architecture of the data exchange service may permit Create and Read, but may not allow Update nor Delete. Since updates may not be permitted, multiple versions of data may be stored and/or the data exchange service may indicate which versions of data are the latest or most up to date. Thus, the deficiencies of normalized data systems from multiple data sources may be addressed by storing the original data, not permitting deletes or updates of data, and/or storing multiple transformations of data. The data exchange service and/or transformation system can be more flexible and/or reliable than normalized data systems that typically integrate data from multiple sources by storing the data in a single format. The systems and methods described herein may enable faster computer processing. For example, streamed processing by the one or more workflows of the transformation system may result in near-time or real-time generated data according to one or more data formats. Accordingly, the processed data in the one or more data formats may be available via the communication interface within seconds of receiving the original data. Further, in some embodiments, the distributed architecture of the workflows of the transformation system and/or the communication interface of the data exchange service may result in faster responses times to requests for data.

Example Data Exchange System

FIG. 1 illustrates an example data exchange service 112, according to some embodiments of the present disclosure. In the example of FIG. 1, the network environment 110 includes a network 122, a data exchange service 112, a user computing device 102, and a provider 104. As used herein, users, user computing devices, providers, and/or location establishments may be referred to as entities. Various communications between these services, systems, and/or devices are illustrated. For example, the user computing device 102 may send and/or receive data from the data exchange service 112, and/or the providers 104 may send and/or receive data from the data exchange service 112. Thus, two or more providers 104 may effectively communicate with one another via the data exchange service 112. Additionally or alternatively, the user computing device 102 may receive data that originally came from a provider 104 and that has been potentially modified by the data exchange service 112.

The example data exchange service 112 includes a communication interface 114, a transformation system 100, and data store(s) 116A-116C. An example of the communication interface 114 is a bi-directional Application Programming Interface (API). Data may be received and/or transmitted to the data exchange service 112 via the communication interface 114. The data may be processed by the transformation system 100 and/or stored in multiple formats in the data store(s) 116A-116C.

In some embodiments, the data exchange service 112, upon receiving data, can dynamically extract, transform, and/or load the data according to one or more customized transformations. As described herein, the data may be transformed in a stream and/or batch process according to multiple customized transformations, such that each consumer of the data may receive the data in a specified format. Moreover, the original data may be stored and/or each transformation of the data may be stored as an audit log. Accordingly, data consumers may receive data within seconds after the initial request due to the near-time or real-time processing of the data that occurs according to one or more specified transformations.

In some embodiments, the systems and methods described herein may be applied in the healthcare context. For example, the data exchange service 112 may be implemented to enable Healthcare as a Service (HaaS). In the example, the dating exchange service 112 may enable healthcare scheduling, messaging, retrieval of patient summary, clinical, and/or analytics data, processing of patient intake forms, physician searching, real or near-time eligibility, payment, demographics, provide a consistent display of healthcare data, ordering of healthcare products, and/or other healthcare services described herein. The bi-directional communication interface and/or data stores of the data exchange service 112 may implement the workflows and/or customized logic for processing patient-related data to enable the healthcare services. Example providers and/or data sources 104 include electronic medical records (EMR) systems, hospital information systems (HIS), radiology information systems (RIS), laboratory information systems (LIS), dietary information systems, picture archiving indication systems (PACS), emergency department and/or room systems, medical transcription systems, and/or some combination thereof. Example EMR systems that may be supported by the data exchange service 112 (via direct database access and/or via the communication interface 114) include Allscripts, IDX, Centricity, and MediTech. Example interfaces, communication protocols, and/or specifications that may be supported by the communication interface 114 include HL7, HL7 over SSL, HL7v2, HL7v3, Minimal Lower Layer protocol (MLLP), Fast Healthcare Interoperability Resources (FIHR), Continuity of Care Document (CCD), Clinical Document Architecture (CDA), Consolidated Clinical Document Architecture (CCDA), Digital Imaging and Communications in Medicine (DICOM), Nationwide Health Information Network (NwHIN) Direct, X12, and/or some combination thereof.

In some embodiments, the data exchange service 112 can include the data stores 116A-116C. The data stores 116A-116C can include a NoSQL database and a search engine. Data may be stored in one or more of the data stores 116A-116C to take advantage of respective benefits for each data store, such as the benefits of particular data store types for optimized writing, reading, and/or searching. The transformation system 100 can include workflows to perform the data processing. Each workflow may include instructions sets to perform the data processing. The data exchange service 112 can receive original data via the communication interface 114. The data exchange service 112 can store the original data in the data stores 116A-116C in its original format. The transformation system 100 can identify the applicable workflows and/or instruction sets to apply to the original data.

A first workflow can generate first data from the original data by applying the first instruction set to the original data. A second workflow can generate second data from the original data by applying the second instruction set to the original data, where the first instruction set differs from the second instruction set. Thus, the transformation system 100 can include customized logic to generate multiple different formats of transformed data from the original data. The transformation system 100 can store the first data and the second data in the data stores 116A-116C, such as the NoSQL database and the search engine.

The data exchange service 112 can receive a first request from a first external computing device via the communication interface 114. In response to the first request, the data exchange service 112 can determine to retrieve the first data from the NoSQL database where, for example, the first request includes an identifier that corresponds to the first data. When compared against other databases, such as relational databases, advantages of NoSQL databases can include that they are more scalable and provide superior performance, and that the data model of NoSQL databases can address several shortcomings of other data models, such as the relational model. The advantages of NoSQL databases include being able to handle large volumes of structured, semi-structured, and unstructured data. The data exchange service 112 can transmit the first data to the first external computing device.

The data exchange service 112 can receive a second request via the communication interface 114. In response to the second request, the data exchange service 112 can determine to retrieve the second data from the search engine where, for example, the second request includes a search parameter. In some embodiments, a search engine can advantageously search data in a table format, such as a table with a large number of rows and/or columns. The data exchange service 112 can transmit the second data to the second external computing device.

In some embodiments, the workflows of the transformation system 100 can include logic determine whether a particular workflow should be applied to data. The first instruction set of the first workflow can include first boolean logic. The transformation system 100 can determine that the original data corresponds to a particular type of data. The transformation system 100 can determine, according to the first boolean logic, to generate the first data because the original data corresponds to the particular type of data. Another workflow can include a different instruction set and different boolean logic, the transformation system 100 can determine, according to the different boolean logic, to not generate data according to a different instruction set because the original data corresponds to the particular type of data.

In some embodiments, advantages of the transformation system 100 storing the original data and/or including workflows to process data is that additional instruction sets and/or workflows can easily be added to the transformation system 100. The transformation system 100 can add a third workflow to the existing workflows. The third workflow can include a third instruction set for processing data. The transformation system 100 can then apply the third workflow to the original data generate third data according to the third instruction set. The transformation system 100 can store the third data in in the data stores 116A-116C.

Figure 2:
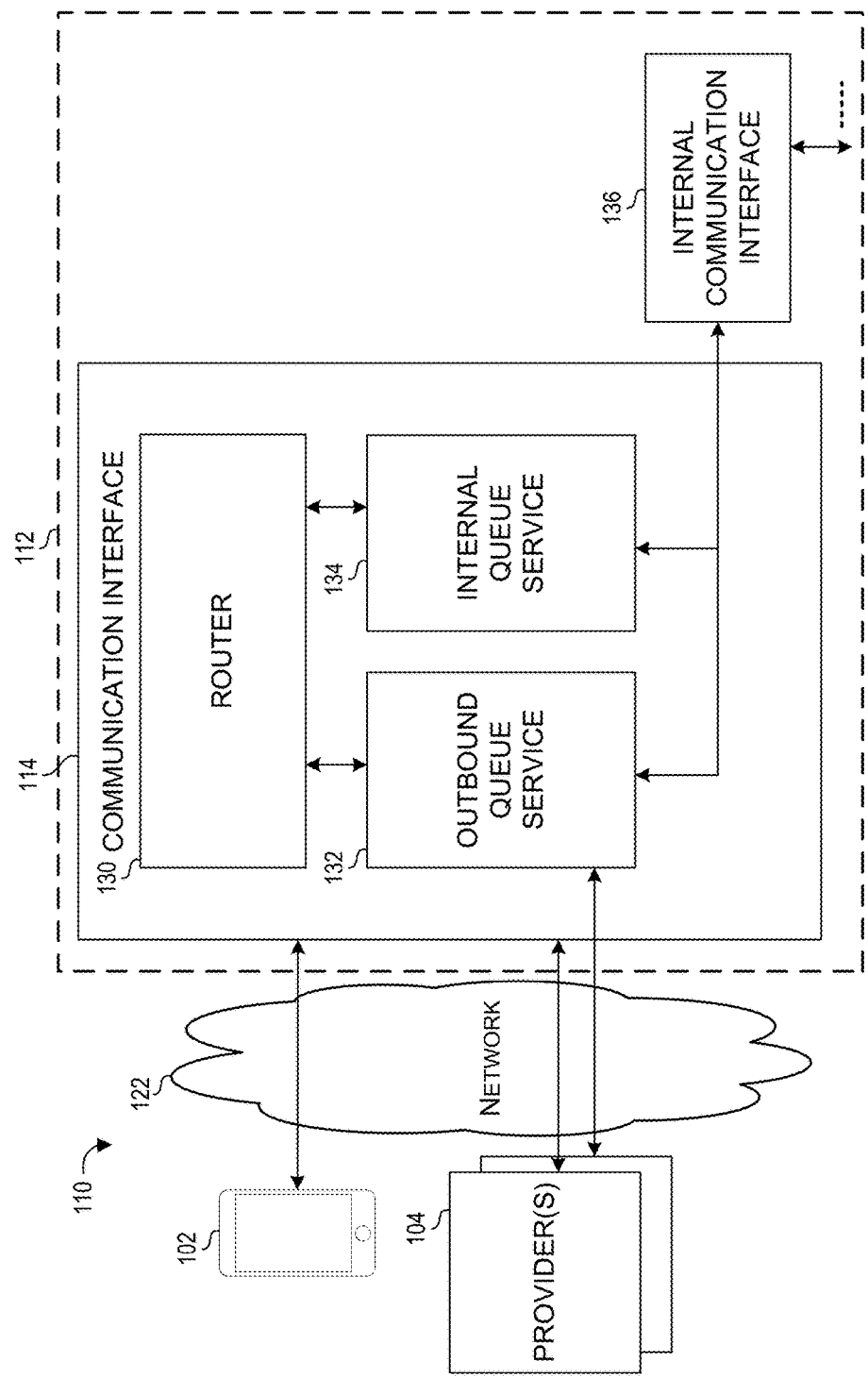
FIG. 2 is a block diagram illustrating another example bi-directional communication system and/or interface.

FIG. 2 illustrates another example data exchange service 112 and communication interface 114, according to some embodiments of the present disclosure. The embodiment of FIG. 2 may be similar to the embodiment of FIG. 1. For example, in the embodiment of FIG. 2, the network environment 110 includes a network 122, a data exchange service 112, a user computing device 102, and a provider 104. The example data exchange service 112 includes an internal communication interface 136, and may include additional elements such as a transformation system and/or data stores (not illustrated). The example communication interface 114 includes a router 130, an outbound queue service 132, and an internal queue service 134.

In some embodiments, the communication interface 114 is load balanced. For example, the communication interface 114 may receive requests, such as HTTP requests. In the example, clients may request through HTTP, DNS, and/or SSL. The router 130 may be load balanced to receive many requests. For example, the router 130 may include many servers, such as in a hosted or "cloud" computing environment, and may use a load balancer, such as NGINX. Thus, the load-balancing of the communication interface 114 may be scaled horizontally (such as adding additional servers) and/or vertically (such as increasing the computing resources of one or more servers). Example load balancing methods include round-robin, a least connection method (a request is sent to the server with the least number of active connections with server weights taken into consideration), an IP hash method (the server to which a request is sent is determined from the client IP address), a generic hash method (the server to which a request is sent is determined from a user-defined key which may be a text, variable, and/or some combination thereof), a least time method (select the server with the lowest average latency and the least number of active connections, where the lowest average latency may be calculated based on one or more parameters, such as time to receive the first byte from the server or time to receive the full response from the server), or some other method. The communication interface 114 may further be implemented to be stateless.

The example router 130 may be a proxy communication interface, such as a proxy API, to communicate with other services. For example, the router 130 may determine where to forward requests and/or data, such as forwarding data to other micro services. The distributed services of the communication interface 130 may use an identity service to communicate with one another. For example, the identity service may use unique service identifiers and/or may authenticate services. In the example, the router 130 may determine whether to forward data to the outbound queue service 132 and/or the internal queue service 134. In some embodiments, the queue services 132 and/or 134 may be load-balanced, such as by using NGINX.

In the outbound queue example, the router 130 has programmatically determined that additional data may be required from an external source. The outbound queue service 132 may send and/or request data from an external provider 104. The outbound queue service 132 then retrieves data and/or receives one or more messages from the external provider 104, such as an external hospital system. The outbound queue service 132 may send a subsequent message to an internal service to transmit the received external data.

In some embodiments, after data has been processed through the queue services 132 and/or 134, the data is transmitted to the remainder of the data exchange service 112 via the internal communication interface 136. For example, the internal communication interface 136 may be an internal API for transmitting data and/or requests to the transformation system 100 and/or data stores 116. Advantages of multiple layers and/or segmentation of services, queues, authentication, and/or messaging systems may include increased security of the data exchange service 112 because this example architecture may require a potential attacker to compromise multiple layers and/or different segments of the data exchange service 112 to successfully penetrate the system.

FIG. 3 depicts example communication interface routines, data types, and/or output, according to some embodiments of the present disclosure. For example, the data exchange service 112 may communicate via the example communication interface routines 310, 312, and 314. In some embodiments, the communication interface routines 310, 312, and 314 may correspond to an API. In some embodiments, the communication interface of the data exchange service 112 may include aspects of representational state transfer (REST) and/or be RESTful. The communication interface may receive and/or return data objects, such as in a JSON or other data format. The communication interface of the data exchange service 112 may further correspond to a framework. An example framework includes a publicly available application programming interface framework. Accordingly, the example APIs may be dynamic. An example API may be dynamically updated via an upload of a configuration file.

The communication interface routines 310, 312, and 314 may correspond to communication specifications of the data exchange service 112. For example, the communication interface routines 310, 312, and 314 may correspond to medication, medical condition, and/or hospital services. In some embodiments, the communication interface routines 310 support HTTP and uniform resource identifiers (URIs). For example, with respect to the communication interface routines 310, one or more medication objects may be retrieved for a user via the GET "/medication" method; a specific medication object may be retrieved via the GET "/medication/:id" method where ":id" corresponds to a parameter; a medication object may be created via the POST method "medication/create"; a specific medication object may be updated via the PUT method "medication/update/:id" where ":id" corresponds to a parameter; and/or a specific medication object may be removed via the DELETE method "/medication/remove/:id" where ":id" corresponds to a parameter. With respect to the communication interface routines 312, a condition may be created via the POST method "condition/create"; and/or a condition may be searched via the GET "/condition/:action" method. As described herein, the data exchange service 112 may support multiple communication interface routines, such as dynamically supporting additional APIs per provider. Additionally or alternatively, the communication interface routines 310, 312, and 314 use and/or support a different communication protocol other than HTTP.

The communication interface routines may receive parameters and/or return output. For example, with respect to the communication interface routines 314, a user's clinical history may be retrieved via the GET method "/hospital/summary/:provider_id". The GET method of the communication interface 314 may include the parameter 320 for a provider_id of parameter type "query" and/or data type "string." The GET method of the communication interface 314 may return output 322. Example output 320 includes a data object, such as a JSON data object. In this example, the output 320 includes data regarding a user's clinical history.

The communication interface routines 310, 312, and 314 may correspond to HTTP method conventions. For example, a GET method may retrieve information from a server as specified by the URI. A POST method may be used to send data to the server as specified by the URI. A PUT method may replace a current representation of the target data object with an uploaded data object as specified by the URI. A DELETE method may remove a current representation of the target data object as specified by the URI. In some embodiments, the data exchange service 112 may support PUT and DELETE methods; however, the underlying implantation of the data exchange service 112 may not follow the CRUD pattern, as described herein. For example, the data exchange service 112 may not actually replace and/or delete data in response to receiving PUT and/or DELETE method invocations.

Figure 4:
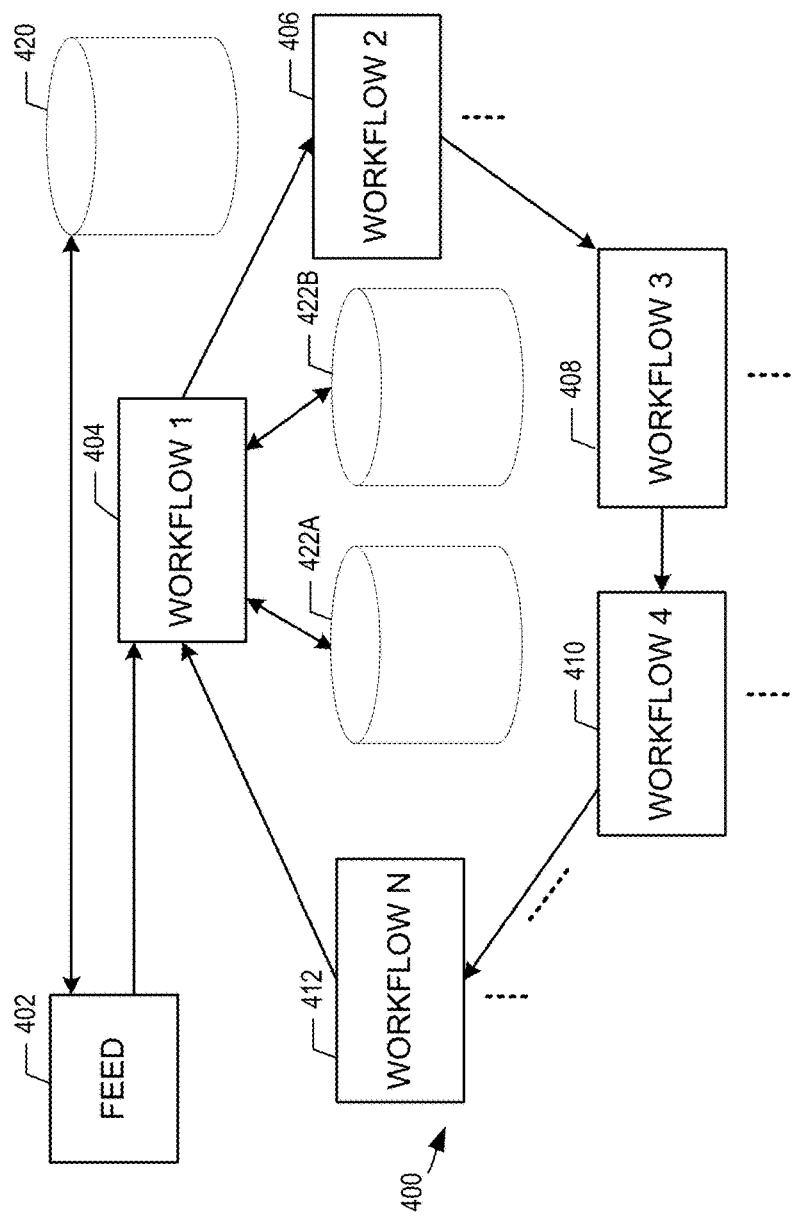
FIG. 4 is a block diagram illustrating another example dynamic extract, transform, and load system.

FIG. 4 is a block diagram illustrating another example dynamic extract, transform, and load system, according to some embodiments of the present disclosure. In the example of FIG. 4, the computing environment 400 includes a feed 402, workflows 404, 406, 408, 410, and 412, and one or more data stores 420 and 422A-422B. The computing environment 400 may correspond to portions of the data exchange service 112. For example, the communication interface 114 of FIG. 1 and/or the internal communication interface 136 of FIG. 2 may correspond to the feed 402. The transformation system 100 of FIG. 1 may include the one or more workflows 404, 406, 408, 410, and 412.

The example feed 402 may receive data in stream and/or batch fashion, as described herein. In a healthcare context, example received data includes ADT, electronic medical records, scheduling, messaging, patient summary, laboratory, clinical, analytics, patient intake forms, physician queries, real or near-time eligibility, payment, demographics (such as patient data including names, addresses, or other patient-related information), healthcare product orders, other healthcare data, and/or some combination thereof. As used herein, the terms "laboratory," "labs," and "lab" may be used interchangeably. Example formats of the received data include HL7, HL7 over SSL, HL7v2, HL7v3, FIHR, CCD, CDA, CCDA, DICOM, PACS, NwHIN Direct, X12, and/or some combination thereof. As an initial matter, a copy of the original data and/or feed data may be stored as originally received in the one or more data stores 420. The feed data is then transmitted to one or more workflows 404, 406, 408, 410, and 412 to process the data.

The one or more workflows process the data and store the generated data in the one or more data stores 422A-422B. For example, a first workflow 404 may include logic, such as boolean logic, to determine whether the received data should be processed by the first workflow 404. Such example logic may include identifying that the received data includes a particular type of data, such as ADT data. Any of the workflows 404, 406, 408, 410, and 412 may be a process in a computation and/or processing system, such as a distributed and/or processing computation system, a streaming computation and/or processing system, a distributed storage system (such as using the MapReduce programming model), and/or some combination thereof. Any of the example workflows 404, 406, 408, 410, and 412 may process data in a near-time or real-time streaming fashion. For example, in a near-time or real-time streaming context, the first workflow 404 may correspond to logic for processing ADT data including a first determination that the received data includes ADT data. The first workflow 404 may initially determine whether the ADT data includes allergy, patient, and/or encounter data. In the allergy example, the first workflow 404 includes an instruction set to parse and/or extract the allergy data according to one or more specifications. The instruction set may include instructions to programmatically generate allergy data according to one or more defined formats. For example, the defined formats may include logic specific to a provider or consumer of the data, and/or that formats the data according to legal or compliance requirements. The processed allergy data is then stored in the one or more data stores 422A-422B. For example, data store 422A may correspond to a distributed database, and/or data store 422B may correspond to a search engine. Additional example data stores include a NoSQL database, a distributed search engine, a RESTful search engine, and/or some combination thereof. The one or more data stores 422A-422B may include multiple of data store types, each of which may be used for respective benefits, such as the benefits of particular data store types for optimized writing, reading, and/or searching. Additionally or alternatively, any of the workflows 404, 406, 408, 410, and 412 may process data in a batch manner. For example, the first workflow 404 may receive unstructured data, which may be queued in batches until sufficient data has been received for processing.

In some embodiments, advantages of the automated processing of the received data according to one or more data formats include improved performance of the data exchange service 112. For example, streamed processing by the one or more workflows 404, 406, 408, 410, and 412 may result in near-time or real-time generated data according to one or more data formats. Accordingly, the processed data in the one or more data formats may be available via the communication interface within seconds of receiving the original data.

In some embodiments, individual transformations and/or steps to process the data may be stored. For example, each instruction and/or operation to generate a data item from the original data may be stored in a data store. Accordingly, a workflow may generate new data by replaying and/or changing some of the previous individual transformations of the data. In some embodiments, the instruction sets for generating the processed data may be dynamic. For example, additional instruction sets may be added to a workflow that enables the workflow to process the original data according to new specifications. In other words, the stored transformation and/or steps allow the data exchange service 112 to optionally "replay" the transformation and/or steps to the original data.

Continuing with the first workflow example, the first workflow may additionally or alternatively process the received data. For example, patient and/or encounter data may be extracted from the ADT data. As used herein, example encounter data includes an in-patient visit at a hospital, clinic, and/or location establishment. If the ADT data includes demographic data, the demographic data may be extracted. Similar to the processing of allergy data, the first workflow may include instruction sets to generate demographic, patient, and/or encounter data according to one or more defined formats. Similarly, the generated data may be stored in the one or more data stores 422A-422B, such as a distributed database, a NoSQL database, a distributed search engine, a RESTful search engine, and/or some combination thereof.

Additionally or alternatively, additional workflows may process the received original data. In some embodiments, the additional workflows may process the data in a similar manner as compared to the first workflow. A second example workflow 406 may be configured to process CCDA data. For example, the second workflow 406 may determine, according to boolean logic, that the original received data includes CCDA data, and that the data should be processed by the second workflow 406. In the second workflow example, the second workflow 406 may extract medication and/or diagnosis data from the CCDA data and generate processed medication and/or diagnosis data in one or more defined formats according to one or more instruction sets. The second workflow 406 can then store the generated data in the one or more data stores 422A-422B. A third example workflow 408 may be configured to process immunization data. Similar to previous examples, the third workflow 408 may: determine to process the original data, such as determining that the original data includes immunization data; extract and/or parse the immunization data, including generating processed immunization data in one or more defined formats according to one or more instruction sets; and/or store the generated data in the one or more data stores 422A-422B. A fourth example workflow 410 may be configured to process labs data. Similar to previous examples, the fourth workflow 408 may: determine to process the original data, such as determining that the original data includes labs data; extract and/or parse the labs data, which may further include pathology, blood bank, and/or microbiology data; generate processed labs, pathology, blood bank, and/or microbiology data in one or more defined formats according to one or more instruction sets; and/or store the generated data in the one or more data stores 422A-422B. As illustrated, the computing environment 400 may process any number of different data formats by additional workflows. For example, additional workflows may be dynamically added to the computing environment 400 and/or the workflows may dynamically receive additional instruction sets for processing and/or generating data according to new data formats.

FIGS. 13A-13M depict example input and/or output of the bi-directional communication system, dynamic extract, transform, and load system, and/or data exchange service. The example input and/or output 1302, 1304, 1306, 1308, 1310, 1312, 1314, 1316, 1318, 1320, 1322, and/or 1324 may correspond to one or more data formats. The example formats of input and/or output 1302-1324 may correspond to HL7, CCDA, and/or JavaScript Object Notation (JSON) data format. Example input and/or output 1302-1324 may be illustrative and may not conform exactly to one or more particular data formats. Moreover, as described herein, additional formats for input and/or output may be supported by the data exchange service 112 and/or the transformation system 100, such as FHIR, DICOM, PACS, NwHIN Direct, X12, XML, or any other data format.

In FIGS. 13A and 13B, the example input and/or output 1302 and/or 1304 may correspond to ADT data. The input data 1302 and/or output data 1304 can include patient data, such as demographics data. The example input 1302 may be in a HL7 data format, which may include delimiters and/or separators such as the pipe (|), caret (^), ampersand (&), and/or tilde (). As described herein, the data exchange service 112 and/or the transformation system 100 may transform the example input 1302 into the example output 1304, which may correspond to a JSON data format. In some embodiments, a workflow, such as the workflows of FIG. 4, may ingest and/or parse the input data into a data object format and/or a key-value pair database. The workflow may then transform the ingested data according to one or more instructions sets. The one or more instruction sets may specify the fields, values, and/or key-value pairs to include in the output data, such as example output 1304. The workflow may also include and/or invoke a formatter that is configured to generate the output data according to one or more formats, such as, JSON, XML, HL7, CCDA, FHIR, a custom format, and/or any other data format. In some embodiments, the output may be enhanced with additional data. For example, the example output 1304 includes an identifier, such as a "patient_id" value, which may be used through the communication interface (such as the API) of the data exchange service 112 to further query, update, and/or transmit data regarding the particular patient. For example, the patient_id may correspond to a data object within the data exchange service 112. In some embodiments, the patient_id may correspond to a stateless data object where the patient_id key may expire after a configurable period of time.

The identifier can include a number, string, and/or randomized string or number. An example identifier is a Globally Unique Identifier ("GUID"). In some embodiments, GUIDs may not be guaranteed to be unique. However, the chances of a repeating unique identifier may be extremely low and/or negligible due to their implementation. For example, a unique identifier may be generated from random or pseudorandom numbers with 122 bits such that the total number of unique identifiers is $2^{122}$. Thus, the unique identifiers are so large that the probability of the same number being generated randomly and/or pseudo-randomly twice is negligible. In some embodiments, shorter and/or longer identifiers may be used.

In FIGS. 13C and 13D, the example input and/or output 1306 and/or 1308 may correspond to CCDA data. The example input 1306 may be in a CCDA data format, may include XML and/or HTML data. The input data 1306 and/or output data 1308 can include medications data. In some embodiments, a workflow, may ingest and/or parse the CCDA input data into a data object format and/or a key-value pair database, which may include parsing the XML and/or HTML data. For example, the workflow may transform the ingested data into the example output 1308, as described herein. Similar to the patient_id described above, the medication_id of the example output 1308 may correspond to a data object that may be used via the communication interface for communication with the data exchange service 112 and/or may expire after a configurable period of time.

In FIGS. 13E and 13F, the example input and/or output 1310 and/or 1312 may correspond to immunization data. The example input 1310 may be in a HL7 data format. As described herein, the data exchange service 112 and/or the transformation system 100 may transform the example input 1310 into the example output 1312, which may correspond to a JSON data format. Similar to the patient_id described above, the immunization_id of the example output 1312 may correspond to a data object that may be used via the communication interface for communication with the data exchange service 112 and/or may expire after a configurable period of time.

In FIGS. 13G-13I, the example input and/or output 1314 and/or 1316A-1316D may correspond to lab data. The example input 1314 may be in a HL7 data format. As described herein, the data exchange service 112 and/or the transformation system 100 may transform the example input 1314 into the example output 1316A-1316D, which may correspond to a JSON data format. Moreover, the instruction sets to transform the example input 1314 may access coded data to match codes in the example input 1314 to some of the output data of the example output 1316A-1316D. Similar to the patient_id described above, the lab_id of the example output 1316A-1316D may correspond to a data object that may be used via the communication interface for communication with the data exchange service 112 and/or may expire after a configurable period of time.

In FIGS. 13J and 13K, the example input and/or output 1318 and/or 1320 may correspond to lab results data. The input data 1318 and/or output data 1320 can include imaging related data. The example input 1318 may be in a HL7 data format. The example input 1318 may include encoded data. For example, the example input 1318 includes encoded base64 data. As described herein, the data exchange service 112 and/or the transformation system 100 may transform the example input 1318 into the example output 1320, which may correspond to a JSON data format. Moreover, the instruction sets to transform the example input 1318 may decode the encoded data. For example, the example output includes "results," which may be the decoded data that was originally encoded in the input. For example, a base64 decoding may be used to generate the decoded HTML data in the example output 1320. According, the decoded HTML may be presented in a user interface by the receiving system of the example output 1320. Similar to the patient_id described above, the imaging_id and/or the encounter_id of the example output 1320 may correspond to a data object that may be used via the communication interface for communication with the data exchange service 112 and/or may expire after a configurable period of time.

In FIGS. 13L and 13M, the example input and/or output 1322 and/or 1324 may correspond to vitals data. The example input 1322 may be in a HL7 data format. As described herein, the data exchange service 112 and/or the transformation system 100 may transform the example input 1322 into the example output 1324, which may correspond to a JSON data format. Moreover, the instruction sets to transform the example input 1322 may omit data from the example input 1322. For example, the example input includes temperature: "99 degrees F. (97.6-100.4)," which may indicate an average or summary temperature (e.g., 99 degrees F.) and a temperature range and/or high/lows (e.g., 97.6-100.4). However, a customized instruction set may include logic to output some data (such as the average or summary temperature, "99° F.") while omitting other data (such as the "97.6-100.4"). Similar to the patient_id described above, the vitals_id of the example output 1324 may correspond to a data object that may be used via the communication interface for communication with the data exchange service 112 and/or may expire after a configurable period of time.

Figure 5:
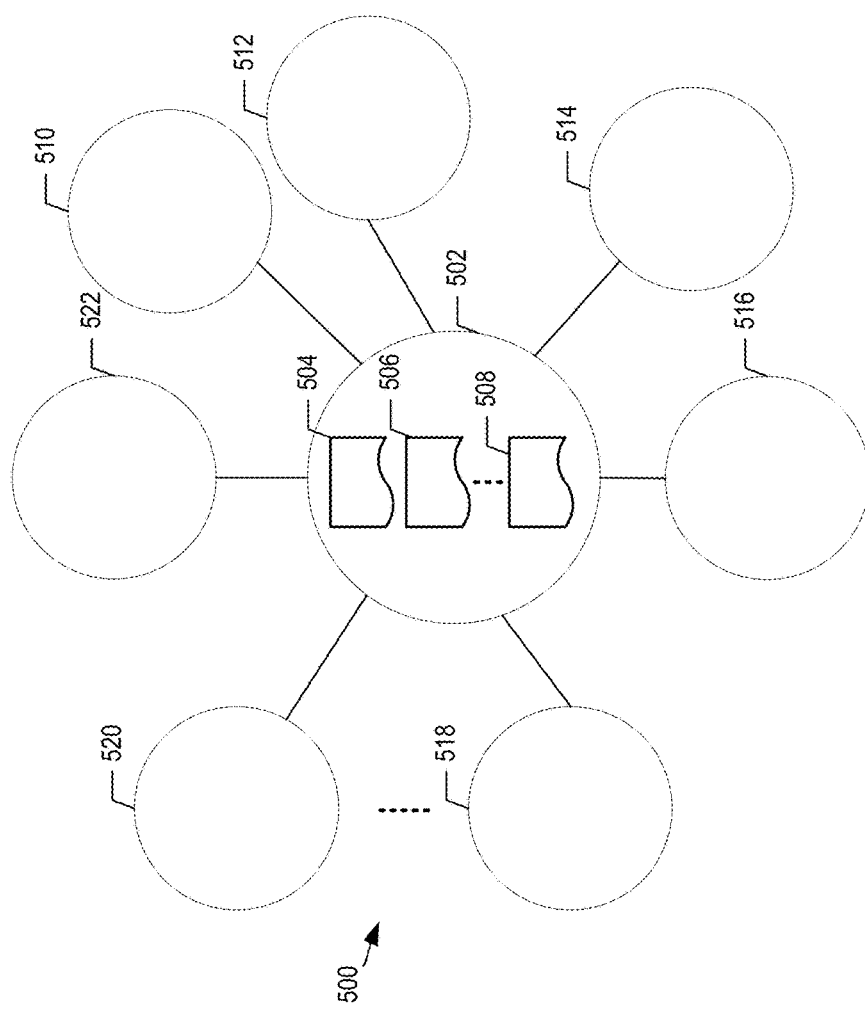
FIG. 5 is a block diagram illustrating an example data schema.

FIG. 5 is a block diagram illustrating an example data schema, according to some embodiments of the present disclosure. The example data schema environment 500 includes data store collections 502, 510, 512, 514, 516, 518, and 520. Each data store collection may include one or more data stores. For example, the data store collection 502 includes data stores 504, 506, and 508. An example data store collection may correspond to a logical grouping of data stores. The example data schema environment 500 may include relations, between the data store collections and/or data stores, which are illustrated as the connecting lines in FIG. 5.

In some contexts, the example data schema environment 500 may correspond to a star pattern in which primary information is centralized that facilitates the access of data radiating outwards from the primary information. The data store collection 502 may represent the center of the example schema. An advantage of this data schema approach may include that the peripheral information may accessed after accessing a minimal number of relations, such as one or two relations, from the primary information. In the healthcare context, the example data schema environment 500 may correspond to a clinical schema. For example, the data stores 504, 506, and 508 of the data store collection 502 may correspond to patient, encounter, and provider data stores, respectively. Accordingly, the data exchange service 112 may use the centralized patient, encounter, and/or provider data to access the data store collections 502, 510, 512, 514, 516, 518, and 520. Example data in the data store collections 502, 510, 512, 514, 516, 518, and 520 may correspond to lab data, pathology data, allergy data, ontology data, microbiology data, immunization data, radiology data, and/or other clinical data. Accordingly, the patient, encounter, and/or provider data may provide identifying information to access other corresponding clinical data, such as lab data, pathology data, allergy data, ontology data, etc.

In some embodiments, the data store collections and/or data stores may include one or more data store types. Example data store collections and/or data stores may correspond to a distributed database, a NoSQL database, a distributed search engine, a RESTful search engine, and/or some combination thereof. In other embodiments, the data schema environment 500 and/or portions of the environment may be in a relational database. For example, data stores 504, 506, and 508 may be tables in a relational database. The results of the data processing described herein may be stored in the data schema environment 500. The data exchange service may use other schemas for storing different types of data. For example, in the healthcare context, a different schema may be used for analytical data.

In some embodiments, the data schema environment 500 and/or data stores of the data exchange service 112 do not follow the CRUD pattern. For example, the underlying data store architecture of the data exchange service 112 may permit Create and Read, but not Update nor Delete. In the example architecture, data is continuously created. Continuing with the example, since updates may not be permitted, multiple versions of data may be stored and/or the data exchange service 112 may indicate which versions of data are the latest or most up to date. In some embodiments, timestamps and/or versioning history is stored for each revision of data, which may indicate the latest and/or most up to date version of the data. Accordingly, the data exchange service 112 may advantageously allow auditing with a high degree of confidence because updates or deletes may be prohibited.

In some embodiments, the data exchange service 112 is configured to automatically generate communication interfaces from data schema. For example, the data exchange service 112 automatically generates technical documentation from the data schema. The technical documentation may correspond to a format that is compatible with a framework for generating communication interfaces, such as a publicly available application programming interface framework. Accordingly, the communication interfaces, such as APIs, may be automatically generated from the technical documentation. The automatically generated communication interfaces can then be used by clients for communicating with the data exchange service 112.

FIGS. 6A-6I illustrate example graphical user interfaces of a user computing device. The graphical user interfaces 600 of FIGS. 6A-6I are example graphical user interfaces of the user computing device 102 of FIGS. 1 and 2. The user computing device may include a client, such as an application, and the application may be configured to communicate with the data exchange service 112. User interactions with the graphical user interfaces 600 of FIGS. 6A-6I may cause the client to request data from the data exchange service 112 and/or to send data to the data exchange service 112. Example data that may be sent and/or received between the user computing device 102 and the data exchange service 112 include the data described in further detail with respect to FIGS. 13A-13M. In some embodiments, the data presented on the user computing device is sent and/or received via the network 122 to the data exchange service 112. Example user interactions include messaging and/or appointment scheduling through the graphical user interfaces 600 of the client. Example presentations of the data include the graphical user interfaces 600 for viewing a patient's health data, such as allergies, medications, conditions, documents, immunization data, and/or vitals. Other aspects of embodiments disclosed herein may be illustrated in FIGS. 6A-6I. In various embodiments, aspects of the user interfaces may be rearranged from what is shown and described below, and/or particular aspects may or may not be included.

Figures 6A, 6B:
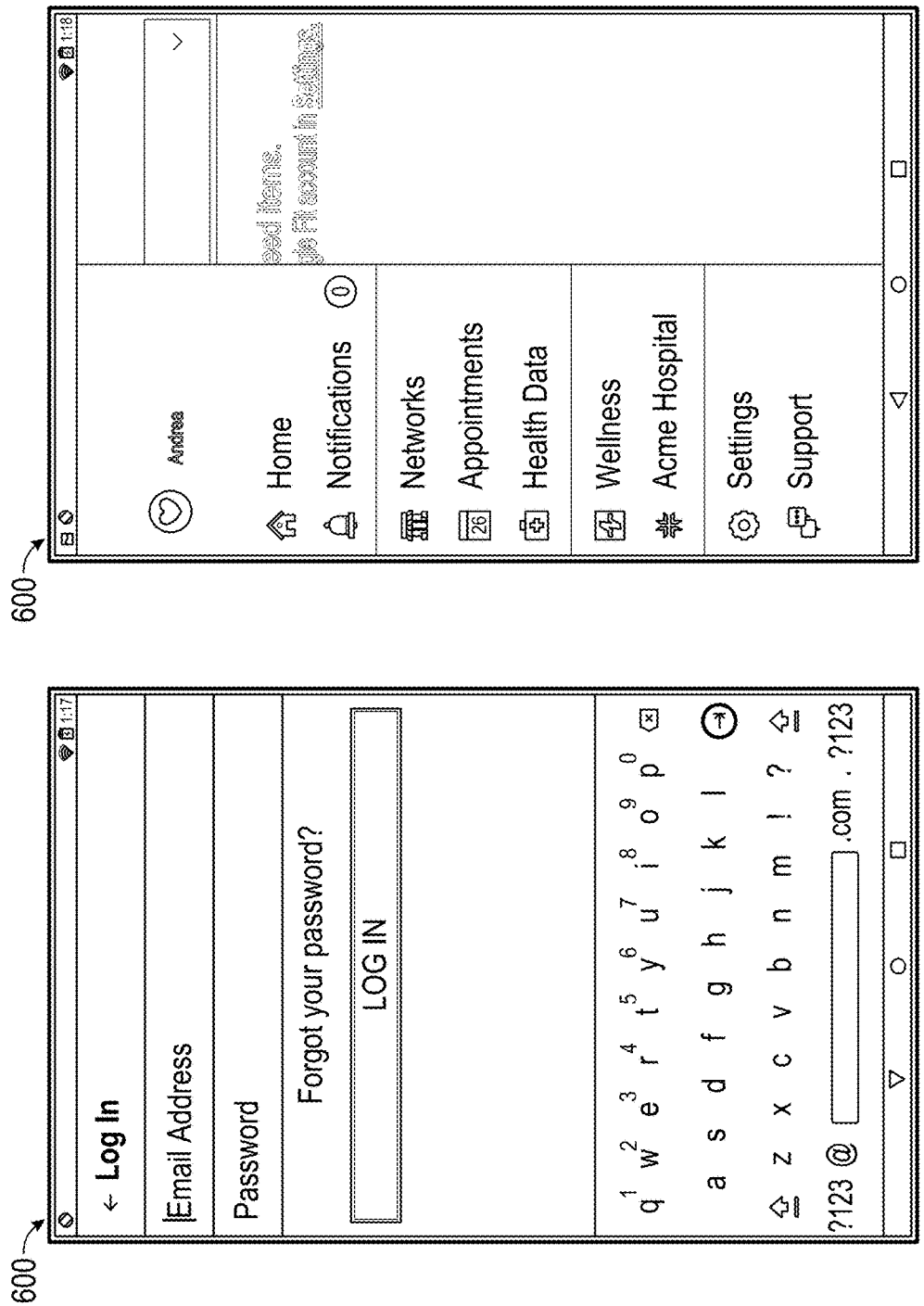

In FIG. 6A, the graphical user interface 600 enables a user login to the client. In some embodiments, the user interaction to login to the client causes bi-directional communication with the data exchange service 112, such as a first transmission from the client to the data exchange service 112 of login credentials and/or a second transmission from the data exchange service 112 to the client authenticating the user. In FIG. 6B, the graphical user interface 600 includes a menu with user interface elements that may be selected.

Figures 6C, 6D:
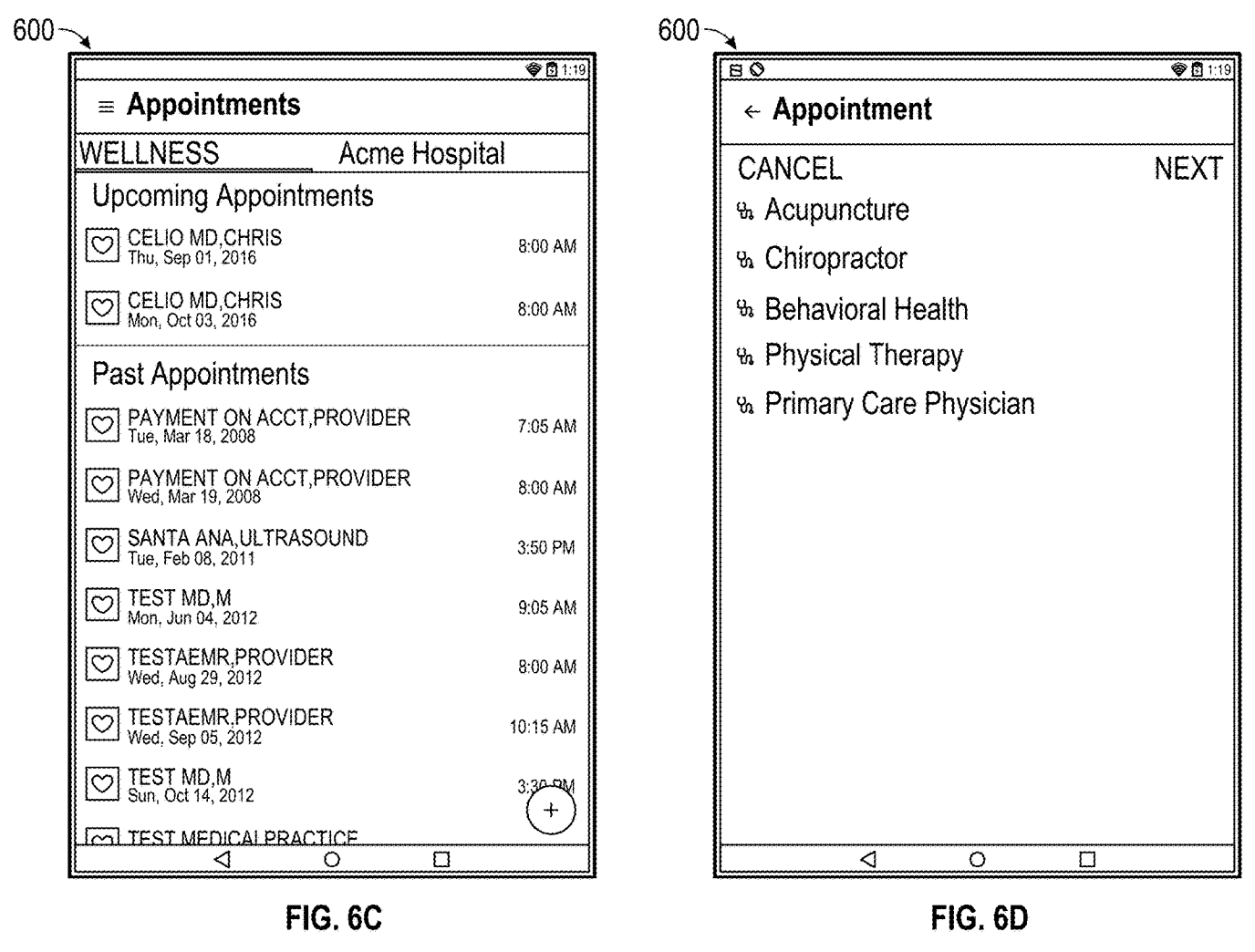

In FIGS. 6C and 6D, the graphical user interface 600 includes user interface elements associated with appointment scheduling. In FIG. 6C, the appointment data presented a graphical user interface 600 may be received from the data exchange service 112. In FIG. 6D, a user may schedule an appointment, which may cause data to be transmitted to the data exchange service 112.

Figure 6I:
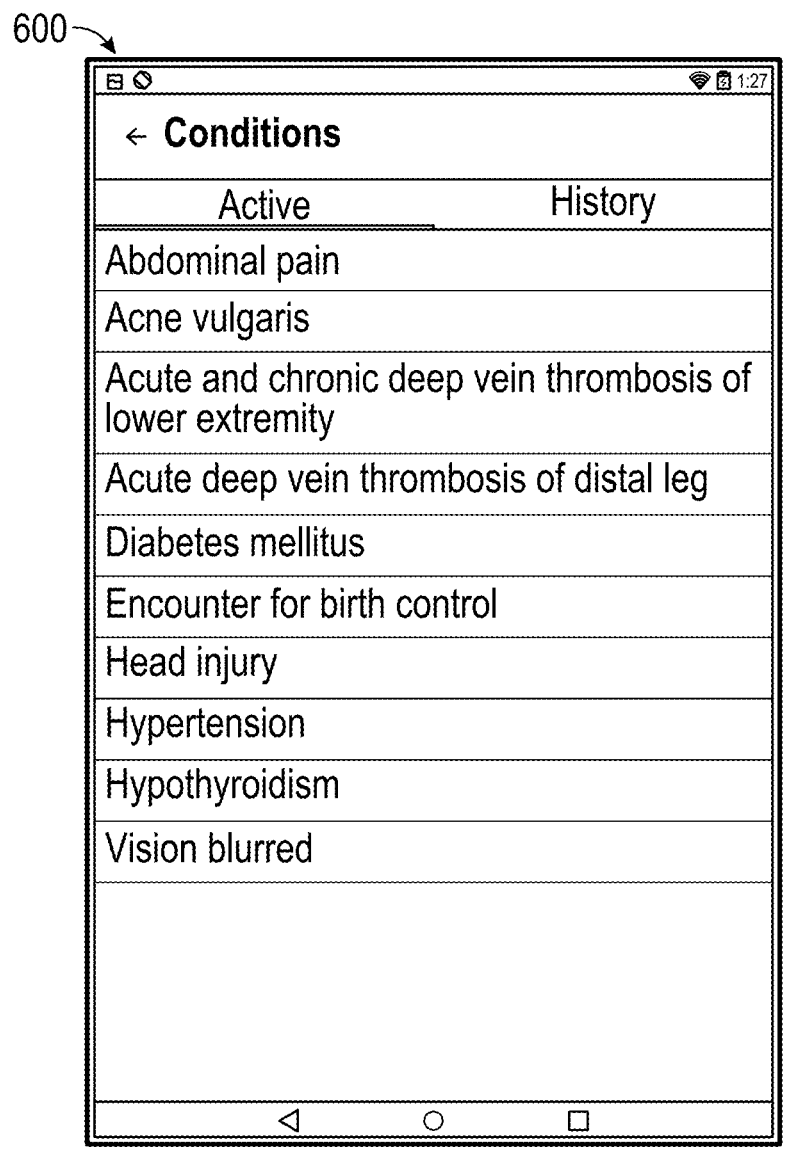

In FIGS. 6E-6I, the graphical user interface 600 enables a user to view health data. In FIG. 6E, user interaction with the graphical user interface 600 may cause the client to request health data from the data exchange service 112. As shown in FIG. 6F, the health data may include allergy data, medications data, conditions data, health-related documents, immunization data, and/or vitals data. In FIG. 6G, example allergy data is presented in the graphical user interface 600. In FIG. 6H, example medications data is presented in the graphical user interface 600, such as active or inactive prescriptions for a particular patient. Example data that may be sent from the data exchange service 112 to the user computing device for presentation in the graphical user interface 600 of FIG. 6H includes the data 1308 described with respect to FIG. 13D. In FIG. 6I, example conditions data is presented in the graphical user interface 600, such as active or past conditions for a particular patient.

FIGS. 9A-9C and 10A-10D illustrate additional example graphical user interfaces of a user computing device. The graphical user interfaces 900 of FIGS. 9A-9C and graphical user interfaces 1000 of FIGS. 10A-10D are example graphical user interfaces of the user computing device 102 of FIGS. 1 and 2. The user computing device may include a client, such as an application, and the application may be configured to communicate with the data exchange service 112. User interactions with the graphical user interfaces 900 of FIGS. 9A-9C and graphical user interfaces 1000 of FIGS. 10A-10D may cause the client to request data from the data exchange service 112 and/or to send data to the data exchange service 112. In some embodiments, the data presented on the user computing device is sent and/or received via the network 122 to the data exchange service 112. Example data that may be sent and/or received between the user computing device 102 and the data exchange service 112 include the data described in further detail with respect to FIGS. 13A-13M. Other aspects of embodiments disclosed herein may be illustrated in FIGS. 9A-9C and 10A-10D. In various embodiments, aspects of the user interfaces may be rearranged from what is shown and described below, and/or particular aspects may or may not be included.

Figures 9A, 9B:
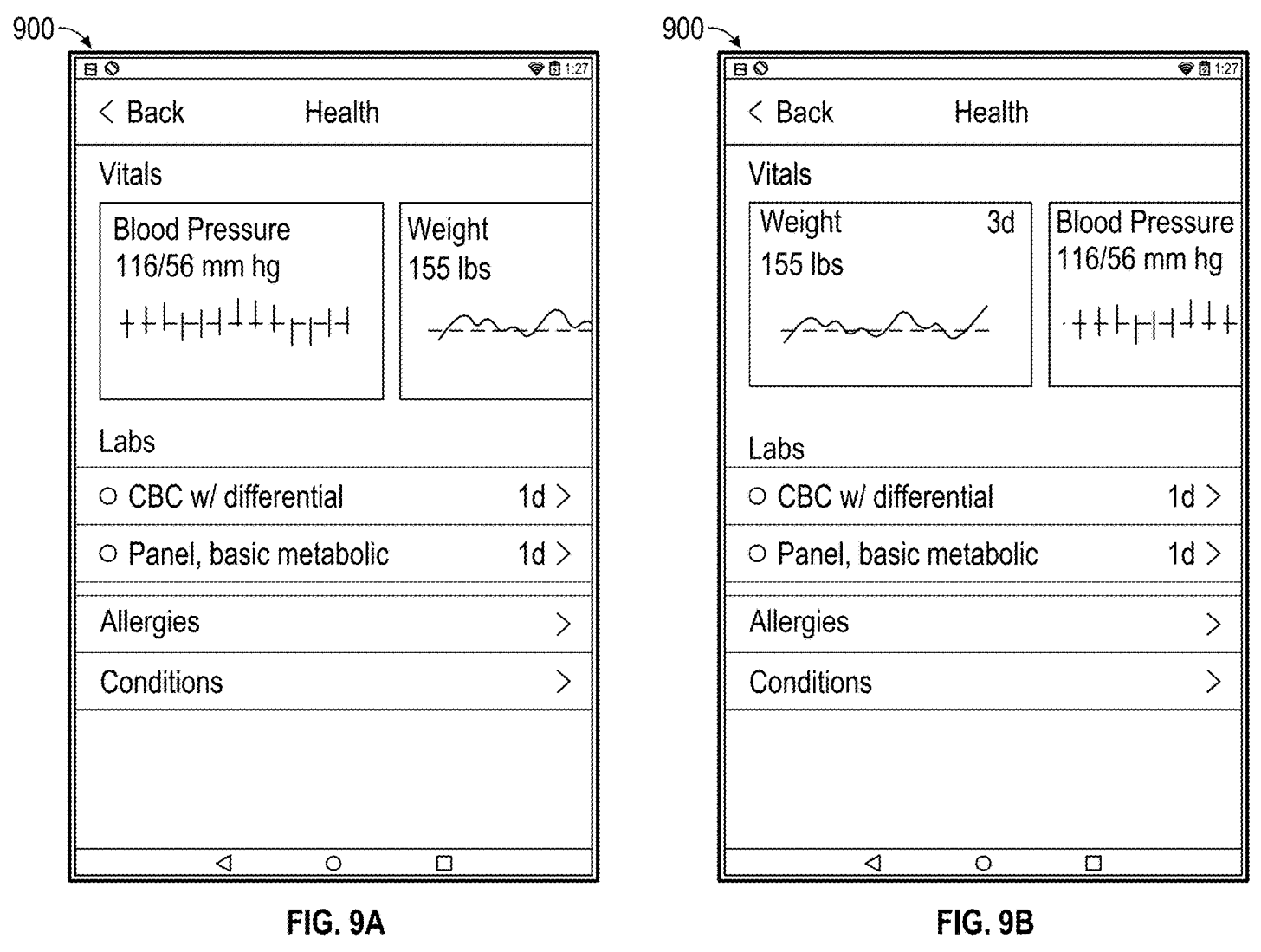
Figure 9C:
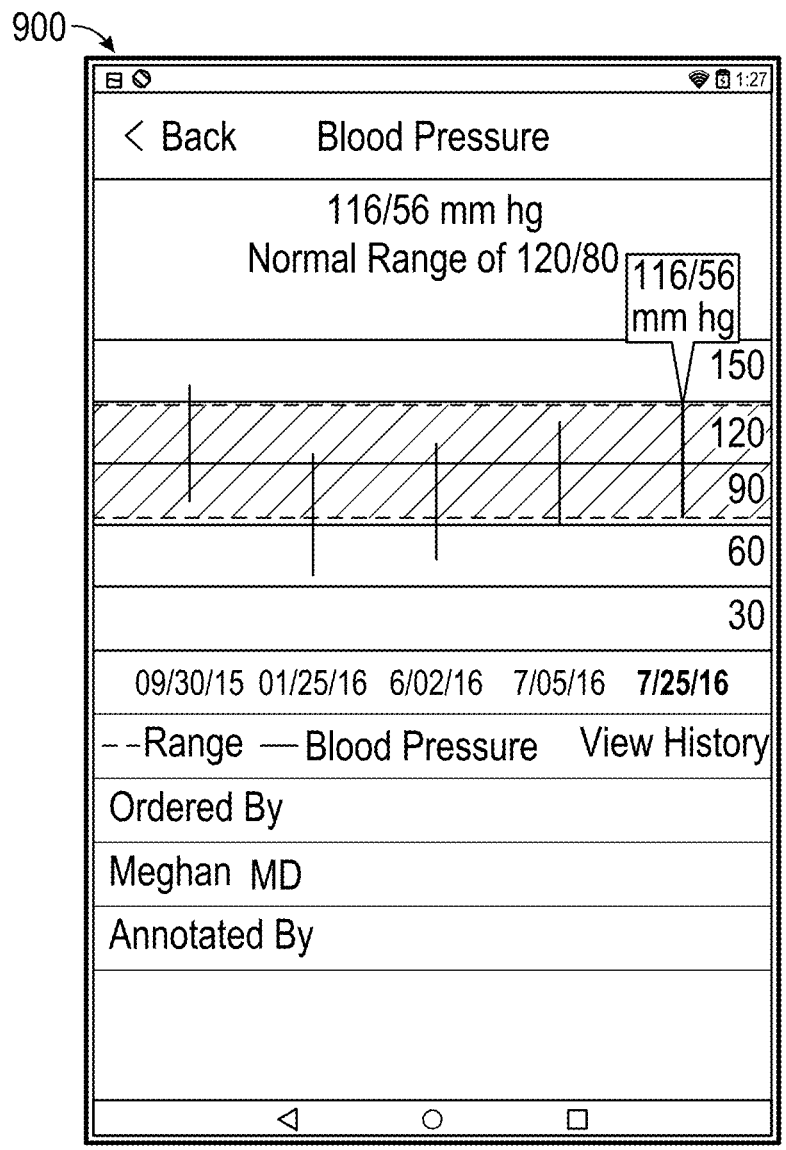
Figures 10A, 10B:
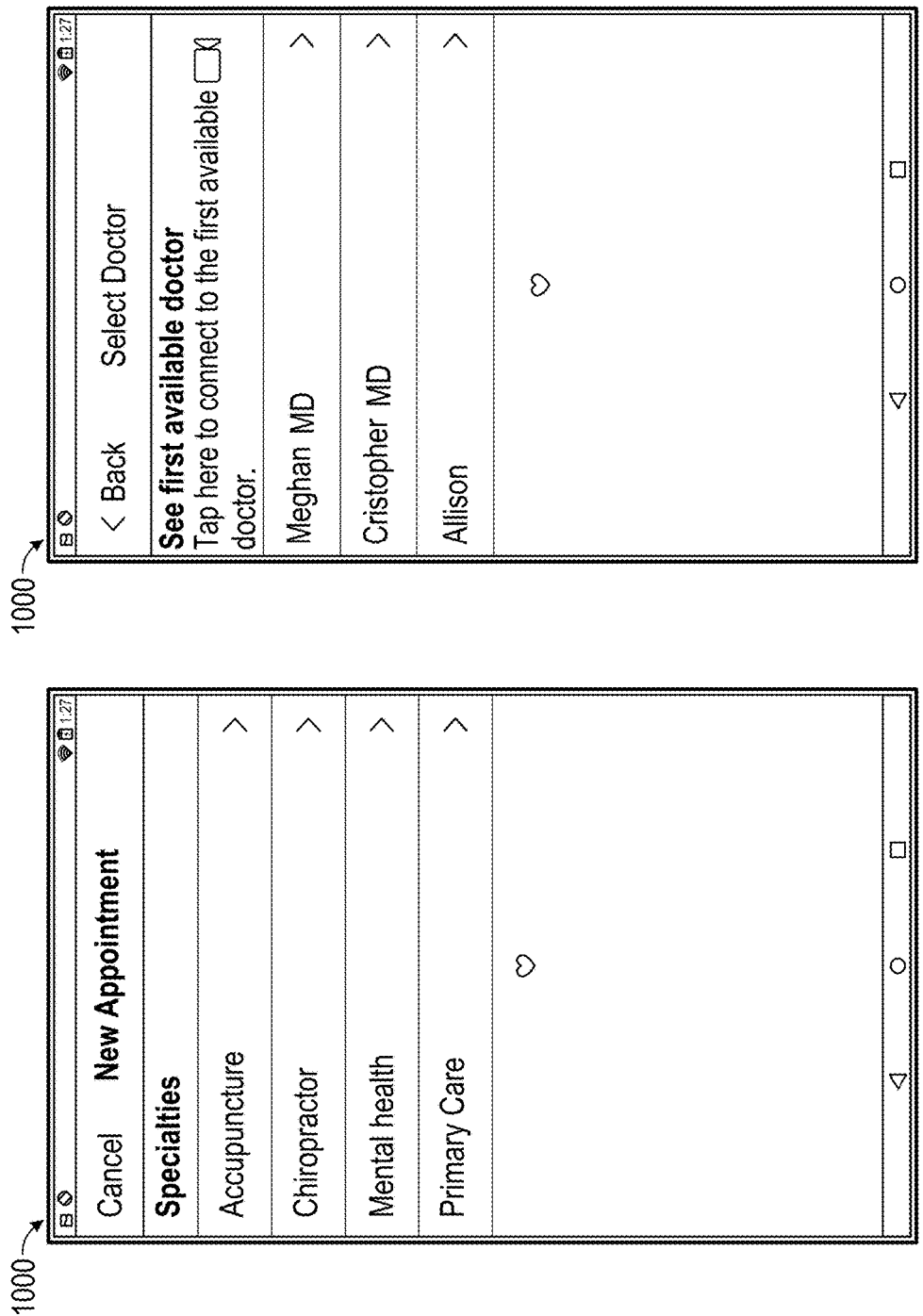

FIGS. 9A-9C depict graphical user interfaces 900 that present a health dashboard. The graphical user interfaces 900 presents vitals data, such as statistics, labs, and medical information that has been recorded and/or collected. The data presented in the graphical user interfaces 900 may be received and/or transmitted from the data exchange service 112. Example data that may be sent from the data exchange service 112 to the user computing device for presentation in the graphical user interfaces 900 of FIGS. 9A-9C includes the data 1324 described with respect to FIG. 13M.

In FIGS. 10A-10D, the graphical user interface 1000 includes additional user interface elements associated with appointment scheduling. In FIGS. 10A-10D, a user may schedule an appointment using the graphical user interfaces 1000, which may cause data to be transmitted to the data exchange service 112.

Figure 7:
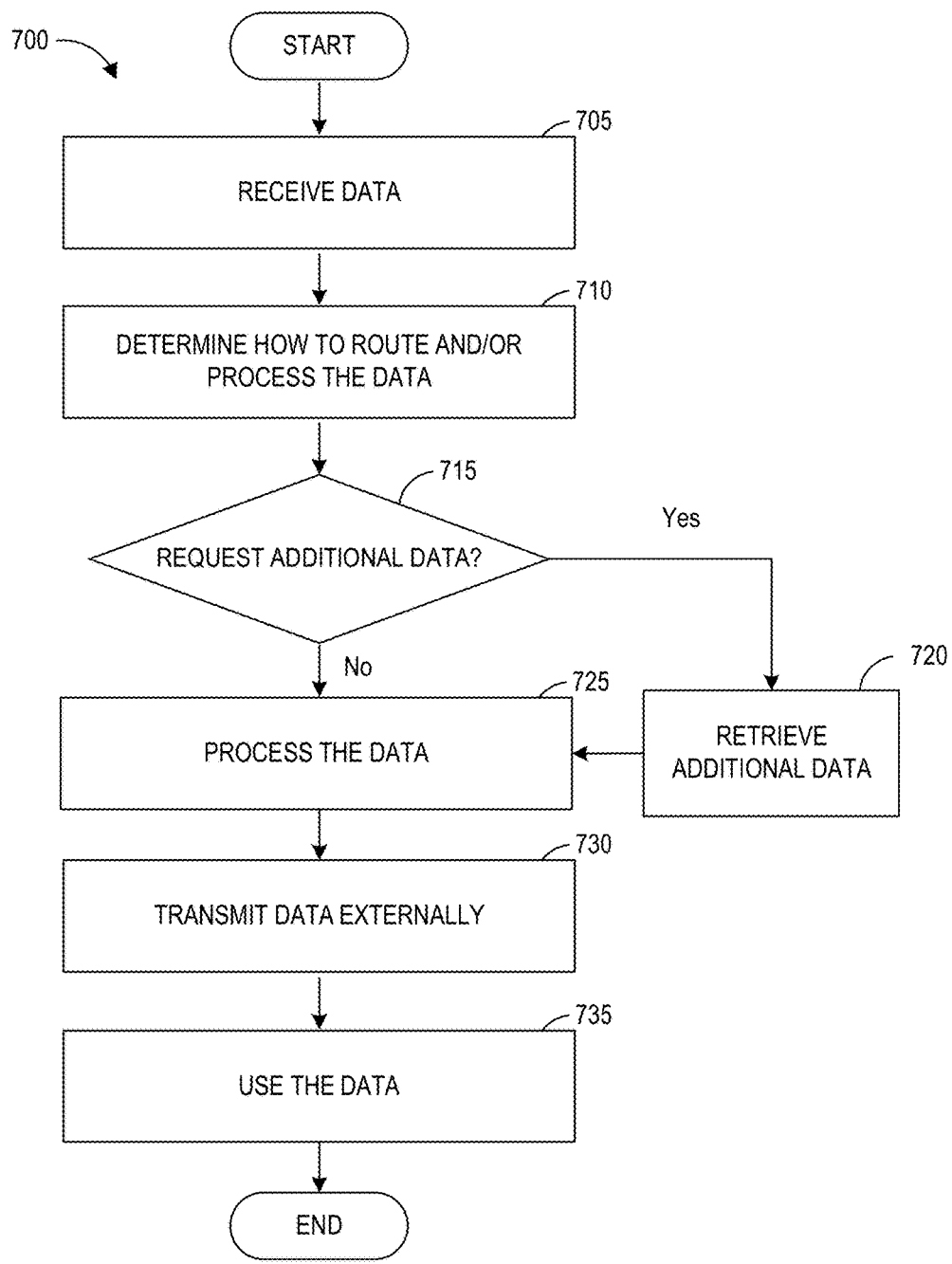
FIG. 7 is a flowchart of an example method of bi-directional communication, data processing, and/or data exchange.

FIG. 7 is a flowchart illustrating an example bi-directional communication, data processing, and/or data exchange process 700, according to some embodiments of the present disclosure. Some blocks of the example method 700 may be performed by portions of the data exchange service 112. For example, the example method 700 may be performed by any of the systems, computing devices, and/or servers described herein, such as the communication interface 114, the transformation system 100, one or more providers 104, and/or one or more user computing devices 102, and/or some combination thereof. Depending on the embodiment, the method 700 may include fewer or additional blocks and/or the blocks may be performed in an order different than is illustrated.

Beginning at block 705, the data exchange service 112 receives data. For example, the data exchange service 112 may receive data via the communication interface 114. In some embodiments, the communication interface 114 includes an API for receiving the data, as described herein. Additional information regarding communication interfaces and/or APIs is described in further detail with respect to FIG. 3. In a healthcare context, example received data includes ADT, electronic medical records, scheduling, messaging, patient summary, laboratory, clinical, analytics, patient intake forms, physician queries, real or near-time eligibility, payment, demographics, healthcare product orders, other healthcare data, and/or some combination thereof. Example formats of the received data include HL7, HL7 over SSL, HL7v2, HL7v3, FHIR, CCD, CDA, CCDA, DICOM, PACS, NwHIN Direct, X12, and/or some combination thereof. Data may be sent over HTTP messages and/or may be sent in the JSON data format. In some embodiments, the data is sent securely. Example security mechanisms include Transport Layer Security (TLS), TLSv2, SSL, HTTPS, and/or VPN. Additionally or alternatively, data may be directly received and/or retrieved from one or more providers. For example, data may be automatically extracted from one or more relational databases, such as a SQL database, and/or electronic medical record systems.

At block 710, the data exchange service 112 determines how to route and/or process the received data. For example, the data exchange service 112 may determine that the received data is ready to be processed internally. Alternatively, the data exchange service 112 may determine that the received data requires further supplementation. Additional information regarding routing of data is described in further detail with respect to FIG. 2 and/or router 130 of FIG. 2. The data exchange service 112 may further use programmatic logic to determine how to process different data. For example, ADT data may be forwarded to a particular workflow for processing, CCDA data may be forwarded to a different workflow for different processing, labs data may be forwarded to yet another workflow for different processing, etc. Additional information regarding workflows and workflow determinations is described in further detail with respect to FIG. 4. In some embodiments, the data exchange service 112 determines to stream and/or batch process the data.

In the batch processing example, the data exchange service 112 will hold the received data until sufficient other data has been received and/or a determination that the received data is complete. For example, the data exchange service 112 first determines whether the received data is complete or incomplete for batch processing. In the example, incomplete data may be identified based on missing parameters and/or identifiers in the data. Example data that requires batching includes unstructured data, which may include an ending and/or segment identifier to indicate whether the received data is complete. The data exchange service 112 may use other logic to determine whether the data is complete. If the received data is incomplete, the data exchange service 112 may hold the received data in a queue until additional data has been received. In the unstructured data example, where a complete portion and/or segment of the data may be necessary before the unstructured data can be structured and/or parsed in a meaningful manner. Example data that may be batched for processing includes laboratory data. In some embodiments, batch processing may advantageously conserve and/or efficiently use computing resources since such processing may require large computing power and batching the processing of the data may result in fewer bottlenecks to spread out the computationally intensive processing.

At block 715, the data exchange service 112 determines whether additional data should be requested. As described herein, the determination may be based on the type of initial data and/or request that has been received. For example, the data exchange service 112 may have in-patient data available internally to be processed through the internal system. However, a request for out-patient data may cause the data exchange service 112 to request specific out-patient data from an external system, such as a healthcare provider. At block 720, the additional data is retrieved externally. For example, the data exchange service 112 may retrieve data directly from an external provider. In other embodiments, the data exchange service 112 sends a message and/or request to the external provider and the external provider sends one or more messages back to the data exchange service 112.

At block 725, the data exchange service 112 processes the data. For example, the transformation system 100 may receive the data. The data may be stored as originally received. The transformation system 100 may include multiple instruction sets for generating new data according to one or more formats, as described herein. As one example, regulations and/or laws may specify the how certain data should be handled. For example, the Health Insurance Portability and Accountability Act ("HIPAA") may indicate that certain information be redacted and/or de-identified. Accordingly, an instruction set may include logic for generating redacted and/or de-identified data. Additionally, other instruction sets may be configured to generate, from the same original data, different data according to other formats and/or logic. Additional information regarding data processing is described in further detail with respect to FIGS. 4 and 5. For example, the generated data sets may be stored in one or more data stores. As described herein, the original and/or processed data may be encrypted when it is stored. The data may be encrypted with a private key. Example encryption algorithms include Triple DES, Blowfish, Twofish, AES, AES-256, AES-256-CBC-HMAC (such as with 4096 bit RSA keys), and/or RSA. The data exchange service 112 may transmit the data internally using cryptographic protocols, such as TLSv2.

At block 730, the data exchange service 112 transmits the data externally. For example, in response to a request, patient data may be transmitted to a user computing device, such as a smartphone and/or desktop. In other examples, data may be transmitted to an external provider, such as a hospital system. In some embodiments, the data is transmitted in response to a communication interface request, such as a request through an API of the data exchange service 112. The data transmission may occur securely over computer networks via the use of security protocols and/or encryption, such as TLS, TLSv2, and/or SSL.

At block 735, the received data is used by a computing device. For example, in the user computing device example, an application on a smartphone and/or a web application may have requested patient data. The user computing device may be accessed by a patient and/or healthcare professional, such as a doctor. The application may present patient medication data, appointment data, patient activity data, acute health data, ambulatory health data, healthcare messages, payment data, eligibility data, and/or any other healthcare service related data. Moreover, via their application, a user may interact with any of their healthcare data, such as requesting medication, sending a message, and/or requesting an appointment, which in turn, further causes additional data to be sent to the data exchange service 112. In other examples, a patient may be discharged from one facility and admitted to another. Accordingly, the receiving facility may request and/or be sent data regarding the new patient via the data exchange service 112.

Figure 8:
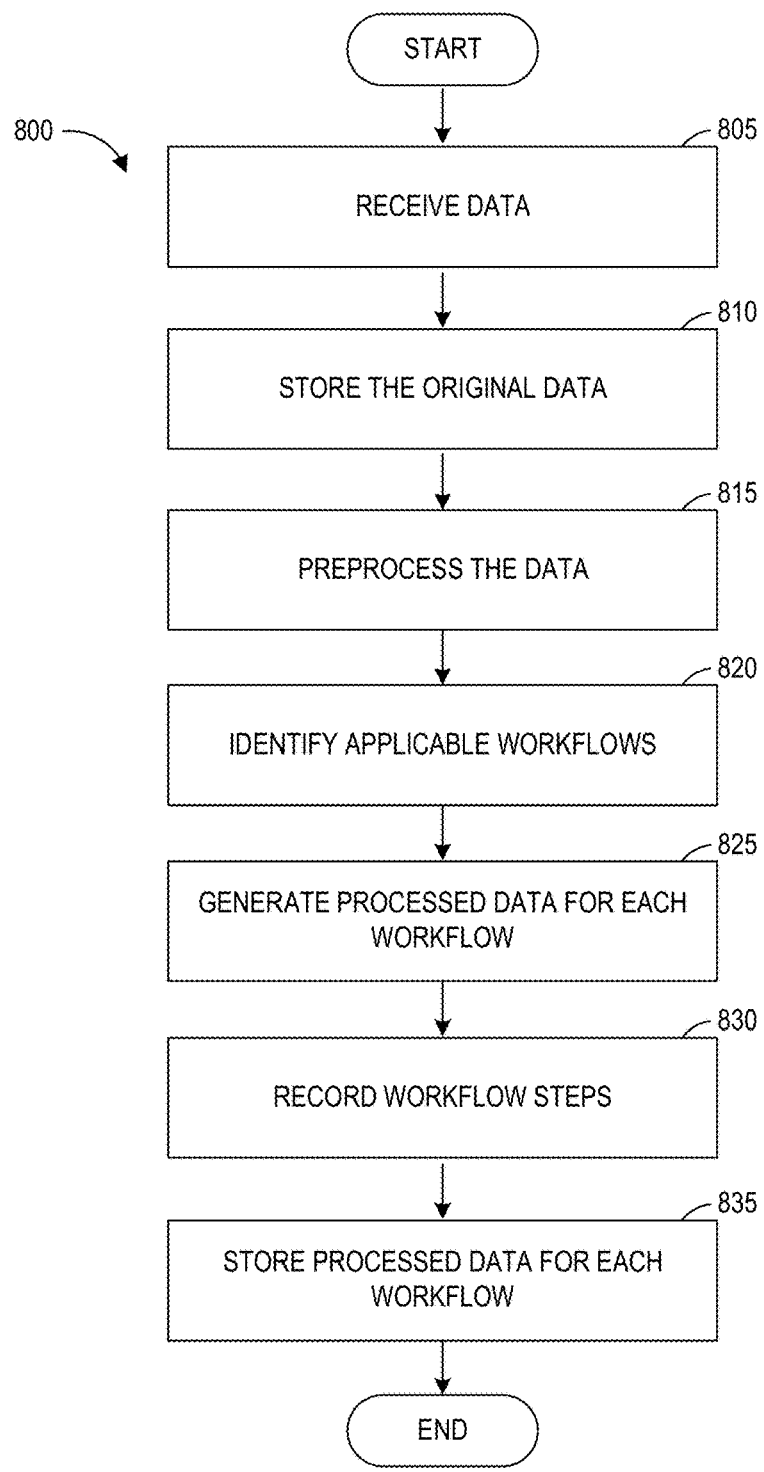
FIG. 8 is a flowchart of an example method of dynamic data transformation.

FIG. 8 is a flowchart illustrating an example dynamic data transformation process 800, according to some embodiments of the present disclosure. Some blocks of the example method 800 may be performed by portions of the data exchange service 112. For example, the example method 800 may be performed by any of the systems, computing devices, and/or servers described herein, such as the communication interface 114 and/or the transformation system 100, and/or some combination thereof. Depending on the embodiment, the method 800 may include fewer or additional blocks and/or the blocks may be performed in an order different than is illustrated. Some blocks of the example method 800 may be similar to blocks of other methods described herein. For example, blocks of the example method 800 may be similar to the blocks of FIGS. 7, 9, and/or 10.

Beginning at block 805, the data exchange service 112 or a component of the data exchange service 112 receives data. For example, block 705 of FIG. 7 may describe in further detail receiving data from an external data source. The data exchange service 112 may implement an internal communication interface for internally transmitting data to the transformation system 100, as described herein. For example, an internal API may be used to transmit data to the transformation system 100. Additional information regarding internally receiving data is described in further detail with respect to FIGS. 2 and/or 4. Additional information regarding communication interfaces and/or APIs is described in further detail with respect to FIG. 3.

At block 810, the transformation system 100 stores the original data. As described herein, advantages of storing the original data may include data integrity and/or robustness of the system to handle additional instruction sets for processing the data, which may be added dynamically. This approach may be in contrast with traditional data normalization systems. An additional advantage of storing the original data is improved auditing. For example, in traditional data normalization systems, if the data is transformed and stored in a single format, the original data and/or format of the data may be lost. Additional information regarding storage of the original data is described in further detail with respect to FIG. 4.

At block 815, the transformation system 100 preprocesses the data. For example, the transformation system 100 may preprocess the data by extracting the data from containers and/or parsing the data. Example containers include JSON wrappers and/or other data formats. Additional example preprocessing of the data by the transformation system 100 includes determining identifying information from the data.

At block 820, the transformation system 100 identifies applicable workflows. The transformation system 100 may include multiple workflows where one or more workflows may process particular data formats and/or types of data. For example, the transformation system 100 may determine that the ADT workflow should process ADT data, the CCDA workflow should process CCDA data, the labs workflow should process labs data, etc. Additional information regarding workflow determinations is described in further detail with respect to FIG. 4. As described herein, each workflow may include multiple instruction sets for generating data according to one or more formats. Accordingly, in some embodiments, the identification of the applicable workflows by the transformation system 100 thereby identifies the applicable instruction sets to process the data.

At block 825, the transformation system 100 generates data for the determined workflows. As described herein, multiple data sets may be generated from the same original data according to respective sets of transformation instructions. In some embodiments, the transformation system 100 applies each of the available and/or compatible instruction sets to generate different sets of data into one or more formats. As described herein, the transformation system 100 generates the data sets in a stream and/or batch fashion. Additional information regarding generating processed data is described in further detail with respect to FIG. 4. As described herein, a workflow may parse the input data, which may be in a particular data format. In some embodiments, the workflow is configured to parse multiple data formats. The parsed data may be stored in a data object and/or data store, such as a key-value database. The available and/or compatible instruction sets may generate output data from the parsed and/or stored data, such as by identifying which of the parsed data should be included in the output data. The available and/or compatible instruction sets may include logic to format the data according to one or more specifications such as number of decimal places, different encodings or decodings, text formats, and/or any other data conventions. The instruction sets may include identifiers that correspond to data objects (such as patient_id, encounter_id, vitals_id, medication_id) for use in the communication interface such as an API. The workflow may include a formatter and/or invoke a formatter to generate the output data according to one or more formats such as JSON, HL7, XML, CCDA, FHIR, a custom data format, and/or any other data format.

At block 830, the transformation system 100 records each of the workflow steps. Continuing with the example where each workflow includes multiple instruction sets for generating data according to multiple formats, each step of an instruction set for generating data may be recorded. An example recorded step may include an individual transformation of a data item, such as converting a data value from six decimal places to three decimal places or redacting a patient name or other identifying information from the generated data. The transformation system 100 may store the workflow steps. For example, the one or more steps may indicate the generation of a new data item from an original data item in the original data. The example one or more steps may indicate an individual transformation of the original data, such as the transformation of an original data item. Example data items include a property, data value, number, string, and/or char value. Additional information regarding storing workflow steps is described in further detail with respect to FIG. 4.

At block 835, the transformation system 100 stores the generated data. For example, the generated data may be stored in one or more data stores. Example data stores include a distributed database, a NoSQL database, a distributed search engine, a RESTful search engine, and/or some combination thereof. In some embodiments, the generated data may be stored with versioning and/or timestamp information. Accordingly, if an entity requests data, the data exchange service 100 may be able to identify the latest and/or previous version of the requested data based on the particular request. Additional information regarding storing the generated data is described in further detail with respect to FIG. 4.

Figure 11:
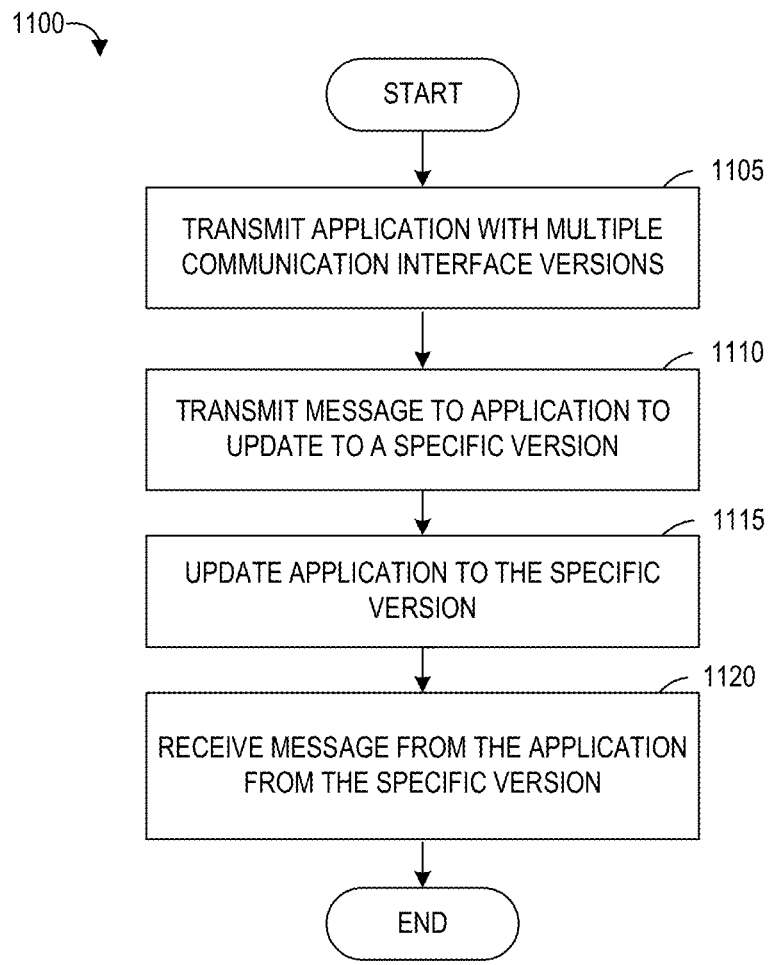
FIG. 11 is a flowchart of an example method of application communication interface version control.

FIG. 11 is a flowchart illustrating an example application communication interface version control process 1100, according to some embodiments of the present disclosure. The data exchange system 112 may use different versions of communication interfaces. Accordingly, the systems and techniques described herein may advantageously facilitate the management of multiple communication interface versions to be simultaneously supported by clients and servers. Some blocks of the example method 1100 may be performed by portions of the data exchange service 112. For example, the example method 1100 may be performed by any of the systems, computing devices, and/or servers described herein, such as the communication interface 114, one or more providers 104, and/or one or more user computing devices 102, and/or some combination thereof. Depending on the embodiment, the method 1100 may include fewer or additional blocks and/or the blocks may be performed in an order different than is illustrated.

Beginning at block 1105, a server may transmit an application and/or an update to an application. For example, an executable application may be downloaded to a user computing device, such as a smartphone. In some embodiments, the application as downloaded and/or installed may include multiple versions of the communication interfaces. For example, there may be multiple versions of the same communication interface. Additional information regarding communication interfaces are described in further detail with respect to FIG. 3. Accordingly, the application as downloaded and/or installed may include the instructions for multiple versions of communication interfaces. However, at a particular time, the application may be configured for a specific version of a particular communication interface.

At block 1110, the data exchange service 112 transmits a message to the application. The example message includes instructions for the application to update to a different version of the particular communication interface. Example advantages of this approach may include: that the application may be upgraded without reinstalling and/or downloading the new communication interface and/or instructions for the new vacation interface; that upgrades may occur transparently to the user; upgrades may be efficiently and compactly communicated to the application; and/or that the data exchange service 112 can simultaneously support multiple versions of communication interfaces. At block 1115, the application upgrades the communication interface to the specified version. At block 1120, the data exchange service 112 receives a message from the application via the upgraded and/or specific version of the communication interface. For example, the new version of the communication interface may send different parameters and/or may use different method calls in communicating with the data exchange service 112.

It will be appreciated that while the present disclosure typically makes reference to information systems in the healthcare context, the systems and methods described herein may be applied to other contexts. For example, the data exchanges, bi-directional interfaces, and/or transformation processes described herein may be applied to different contexts dealing with large amounts of data, such as accounting, retail, analytical, finance, energy, etc. Any transactional data set may be supported by some embodiments of the data exchange service described herein. Particular example contexts include data exchanges for financial services, such as pension funds, or an energy context like the oil industry.

Additional User Computing Device Examples

The data exchange service 112 may communicate with a user computing device. For example, the data exchange service 112 may send and/or receive data from a user computing device 102, as described with respect to FIG. 1. The example user computing device 102 may be a tablet. Form data may be sent and/or received between the data exchange service 112 and the user computing device 102. Authentication and/or authorization data may be transmitted between the data exchange service 112 and the user computing device 102. Signature data may be transmitted between the data exchange service 112 and the user computing device 102. The systems and techniques described herein may be applied in a person-intake and/or healthcare example. For example, a new patient may need to submit form data at a healthcare establishment, such as a clinic or a hospital. A user may be prompted to setup and/or update their profile and/or demographic information within the data exchange service 112 by submitting the form data. After a user has submitted form data once, they may not need to submit form data on subsequent visits unless data has changed. In some embodiments, the form submission data and/or other personal information is not stored on the user computing device, but rather is transmitted to the data exchange service 112 or other services. Advantages of a form submission system including the data exchange service 112 and/or the user computing device 102 include reducing or eliminating paperwork and/or decreasing waiting times to complete an intake. Further, the application on the user computing device 102 may include security protocols to log out of the application. Thus, since form submission data and/or other personal information is not stored on the user computing device 102, if the user computing device 102 is stolen, then no form submission data and/or other personal information can be compromised.

FIGS. 14A-14M illustrate additional example graphical user interfaces of a user computing device. The graphical user interfaces 1400 of FIGS. 14A-14M are example graphical user interfaces of the user computing device 102 of FIGS. 1 and 2. The user computing device may include a client, such as an application, and the application may be configured to communicate with the data exchange service 112. User interactions with the graphical user interfaces 1400 of FIGS. 14A-14M may cause the client to request data from the data exchange service 112 and/or to send data to the data exchange service 112. In some embodiments, the data presented on the user computing device is sent and/or received via the network 122 to the data exchange service 112. Example data that may be sent and/or received between the user computing device 102 and the data exchange service 112 include the data described in further detail with respect to FIGS. 13A-13M. Example user interactions include providing user input, such as form and/or signature data, to complete a user check-in process. Other aspects of embodiments disclosed herein may be illustrated in FIGS. 14A-14M. In various embodiments, aspects of the user interfaces may be rearranged from what is shown and described below, and/or particular aspects may or may not be included.

In FIG. 14A, the graphical user interface 1400 enables a user to begin the check-in process. As illustrated, a user can input an authentication or PIN code to login. In other embodiments, a user may be prompted to check in with a username and password (not illustrated). In FIG. 14B, the graphical user interface 1400 presents an appointment schedule. A user, such as the patient or check-in clerk, can select a particular appointment for a patient in the appointment schedule.

In FIGS. 14C, 14D, 14E, 14F, and/or 14G, the graphical user interface 1400 enables a user to enter user input that can include demographics data. The user computing device may transmit the user input, which can include demographics data, to the data exchange service 112. Example demographics data includes an email address, one or more phone numbers, one or more physical addresses, race or ethnicity, one or more languages, emergency contact information, guardian information, and/or any other kind of information associated with a patient. Example data that may be sent from the data exchange service 112 to the user computing device for presentation in the graphical user interfaces 1400 of FIGS. 14D-14G includes the data 1304 described with respect to FIG. 13B.

Figure 14I:
Figure 14J:
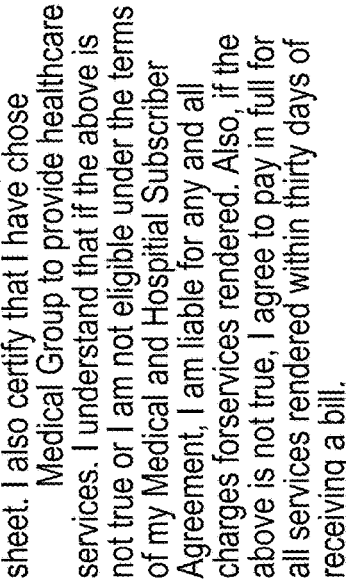

In FIGS. 14H-14J, the graphical user interface 1400 enables a user to submit signature data. In FIG. 14I, a user can submit the input signature 1402. In some embodiments, the user computing device can process the input signature 1402, which may be in an image format, to generate signature data. The signature data may be in a scalable vector graphic (SVG) data format. The user computing device can transmit the signature to the data exchange service 112. Additionally or alternatively, the input signature 1402, which may be in an image format, may be transmitted to the data exchange service 112 and the data exchange service 112 may process the input signature 1402 to generate signature data, which may be in a scalable vector graphic (SVG) data format.

In FIG. 14J, a user can submit the input signature 1404. As described herein, the signature data for the signature 1404 may be generated from the signature 1402 of FIG. 14I. For example, the signature 1404 may be in a scalable vector graphic (SVG) data format.

Figure 14K:
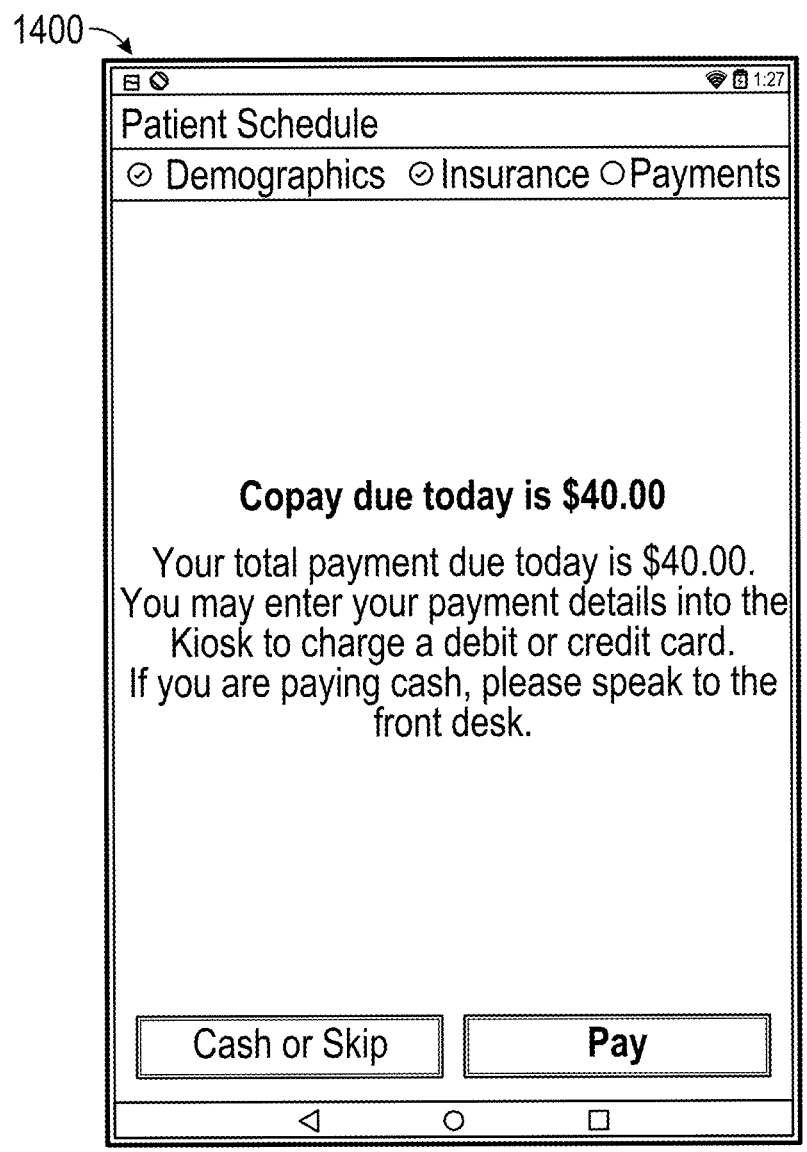

In FIGS. 14K, 14L, and/or 14M, the graphical user interface 1400 enables a user to submit payment data and complete the check-in process.

In some embodiments, the data exchange service 112 and the user computing device 102 communicate through a communication interface, as described herein. For example, the data exchange service 112 and the user computing device 102 communicate through communication interface routines, HTTP requests and responses, and/or URIs, which are described in further detail with respect to FIG. 3. For example, the demographic information corresponding to the forms of FIGS. 14A-14K may be sent via a communication interface routine and/or API call to the data exchange service 112. Other gathered information, such as the information shown in FIGS. 14A-14K, may be sent via other communication interface routines and/or API calls to the data exchange service 112 or other services.

In some embodiments, other check-in techniques may be used additionally or alternatively to what is shown in FIGS. 14A-14M. For example, a user may be prompted to check in with a username and password. Additionally or alternatively, the username and password check-in may occur via a separate application and/or user interface, such as the application and/or user interface of FIGS. 6A-6I. In other embodiments, the user computing device of the person checking in, which may have an application running on it, may communicate with the user computing device of the staff person to authenticate the user. The authentication communication between the devices may occur automatically via Bluetooth or other wireless communication technology. In other embodiments, the application of the user computing device of the person checking in may receive an authentication or PIN code from the data exchange service 112, and the user may present the authentication or PIN code to the staff person to check the user in and/or identify the user.

Figure 15:
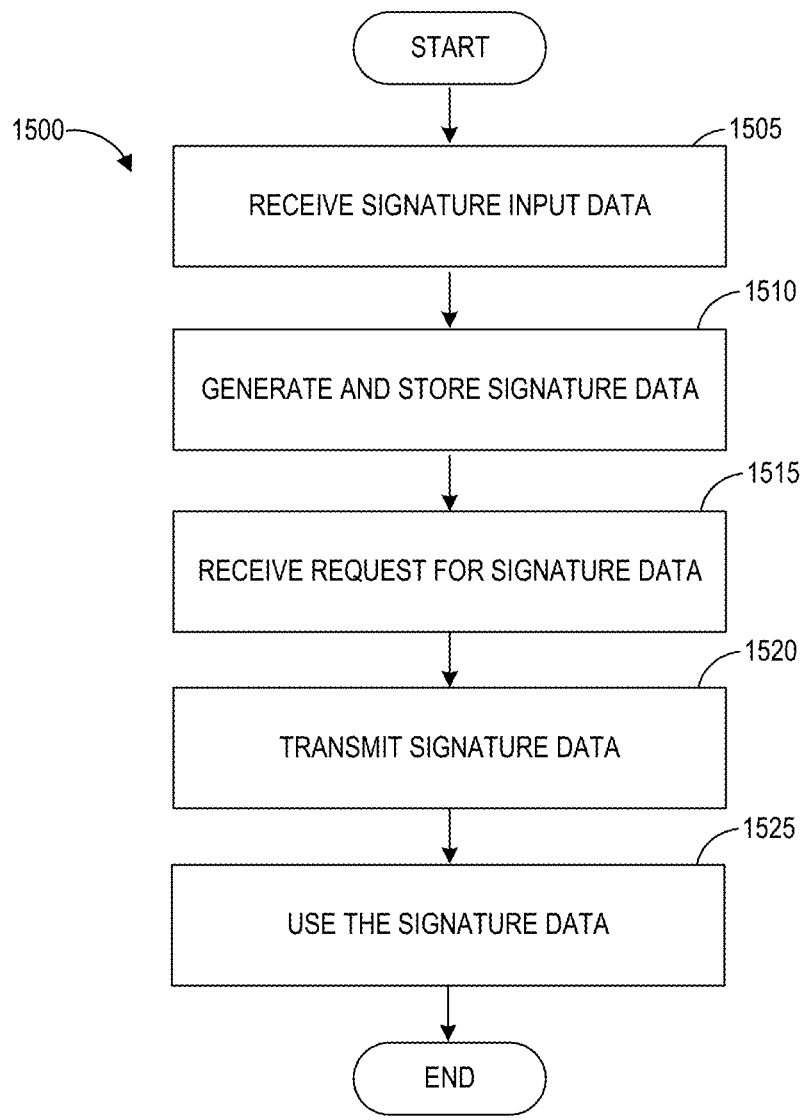
FIG. 15 is a flowchart of an example method of signature generation.

FIG. 15 is a flowchart illustrating an example signature submission process 1500, according to some embodiments of the present disclosure. Some blocks of the example method 1500 may be performed by portions of the data exchange service 112 and/or the user computing device 102. The example method 1500 may be performed by any of the systems, computing devices, and/or servers described herein. Depending on the embodiment, the method 1500 may include fewer or additional blocks and/or the blocks may be performed in an order different than is illustrated. Some blocks of the example method 1500 may be similar to blocks of other methods described herein.

Beginning at block 1505, the data exchange service 112 or an application may receive signature input data from the user computing device 102. The user computing device 102 may receive signature input data 1402 of FIG. 14I from a user. The signature input data may be in an image or other data format. Example image formats include png, jpeg, bmp, etc.

At block 1510, the data exchange service 112 or an application generates signature data from the signature input data. For example, the data exchange service 112 may execute an algorithm to generate scalable vector data from the signature input data. Example algorithms include Bezier curve fitting and/or Bezier linear regression to generate the signature data. An example data format for the signature data includes a scalable vector graphic (SVG) data format. Advantages of the signature data format include that the signature can be reproduced to scale, which may not be possible with image formats such as png, jpeg, bmp, etc. The data exchange service 112 may store the signature data with the user's account and/or profile for later use.

At block 1515, another service or the user computing device 102 may request the signature data. As described herein, the request may be sent via the communication interface and/or APIs described herein. Further, the request may include information that authenticates the user for which the signature request is associated.

At block 1520, the data exchange service 112 or an application transmits the signature data to the service or the user computing device 102 that requested the data. At block 1525, the service or the user computing device 102 may use the signature data. For example, the service or the user computing device 102 may apply the user's stored signature, which is in a scalable format, instead of requiring the user to manually sign multiple times. As shown in FIG. 14J, the signature data can be applied multiple times. Further, the data exchange service 112 and/or another service may convert the signature data into another format, such as a Portable Document Format (PDF). In the example, the data exchange service 112 and/or another service may transmit the other signature format and/or the PDF signature to another system, such as an EMR system, which requires the format.

Figure 16:
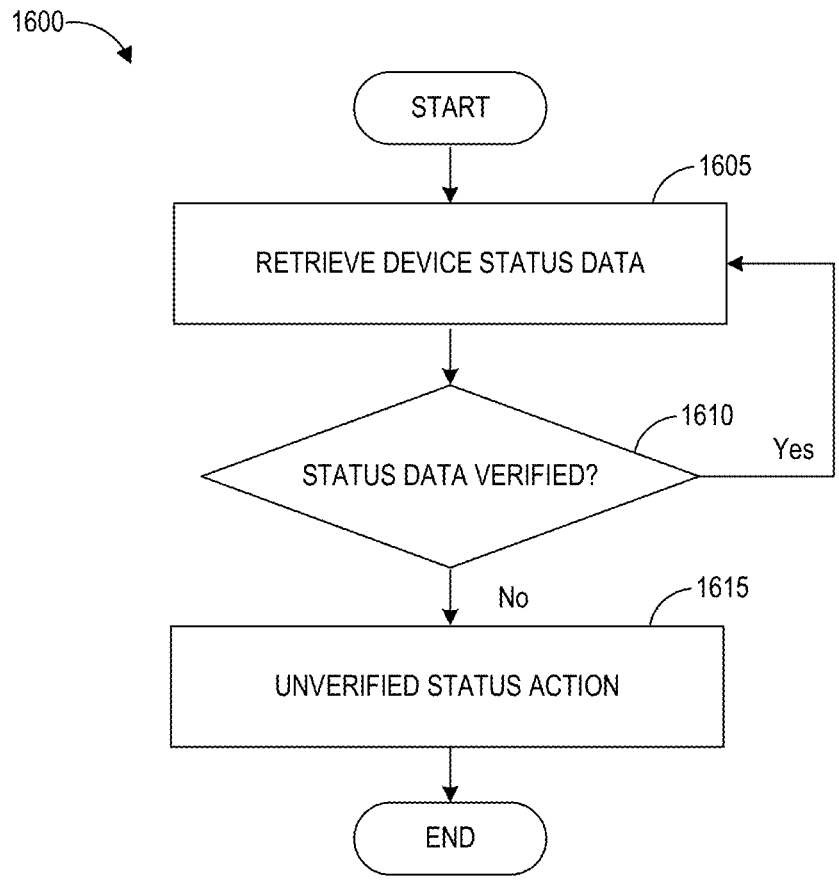
FIG. 16 is a flowchart of an example method of device status verification.

FIG. 16 is a flowchart illustrating an example device verification and/or security process 1600, according to some embodiments of the present disclosure. Some blocks of the example method 1600 may be performed by portions of the user computing device 102. The example method 1600 may be performed by any of the systems, computing devices, and/or servers described herein. Depending on the embodiment, the method 1600 may include fewer or additional blocks and/or the blocks may be performed in an order different than is illustrated. Some blocks of the example method 1600 may be similar to blocks of other methods described herein.

Beginning at block 1605, the user computing device 102 and/or an application of the user computing device 102 retrieves device status data. Example device status data includes wireless connectivity data, network data, and/or geographic and/or geolocation data. For example, the wireless connectivity data may include the Service Set Identifier (SSID) or hotspot that the user computing device 102 is connected to or the default and/or configured SSID. The example network data includes data packets that are received from a computing network, which may correspond to one or more network protocols such as HTTP, TCP/IP, etc. Example geographic and/or geolocation data includes Global Positioning System (GPS) data.

At block 1610, the user computing device 102 and/or the application determines whether the device status data is verified. In one example, the user computing device 102 and/or the application determines whether the user computing device 102 is still connected to the predefined SSID. For example, the predefined SSID may be "Establishment1Network," and if the user computing device 102 is stolen or removed from the establishment, eventually the user computing device 102 will disconnect from the SSID "Establishment1Network." As another example, the network data may indicate a MAC address that the user computing device 102 is connected to, such as a gateway or router device. In the MAC address example, if the user computing device 102 is stolen or removed from the establishment, the user computing device 102 may receive a packet from another gateway or router device that has a different MAC address than the MAC address that the user computing device 102 is configured for. In the geographic and/or geolocation data example, the application may have a home location and/or a permitted operating area, such that the application may determine if the user computing device 102 leaves a predefined distance from the home location and/or a predefined area, such as a radius area. Accordingly, the application may store verification data, such as the SSID, network data, and/or geographic and/or geolocation data to verify the device status data.

If the device status data is verified, then the application may return to block 1605 to retrieve updated device status data. In this manner, the application can continuously poll to verify the status of the user computing device 102. In some embodiments, the continuous loop or polling may occur after a predefined or configurable time interval, such as every second, 30 seconds, 1 minute, 5 minutes, etc.

At block 1615, if the device status data is unverified, the user computing device 102 and/or the application takes an unverified status action. In some embodiments, the device status data may be unverified if the device status data is incomplete. For example, if a wireless, network, or GPS device of the user computing device 102 is disabled, then the application may treat the device status data as unverified. An example unverified status action includes logging a staff person or entity out from the application. Accordingly, if the user computing device 102 leaves the establishment or is stolen, the thief would not be able to access the application without entering a proper authentication code. Further, the application may not store or persist any confidential, personal, or any form data, which is an additional security feature if the user computing device 102 is stolen or goes missing. Other unverified status actions include locking or bricking the user computing device, sending an alert message electronically to the data exchange service 112 or another system, and/or generating another type of alert or alarm, such as an alarm noise.

Example Implementation Mechanisms

Figure 12:
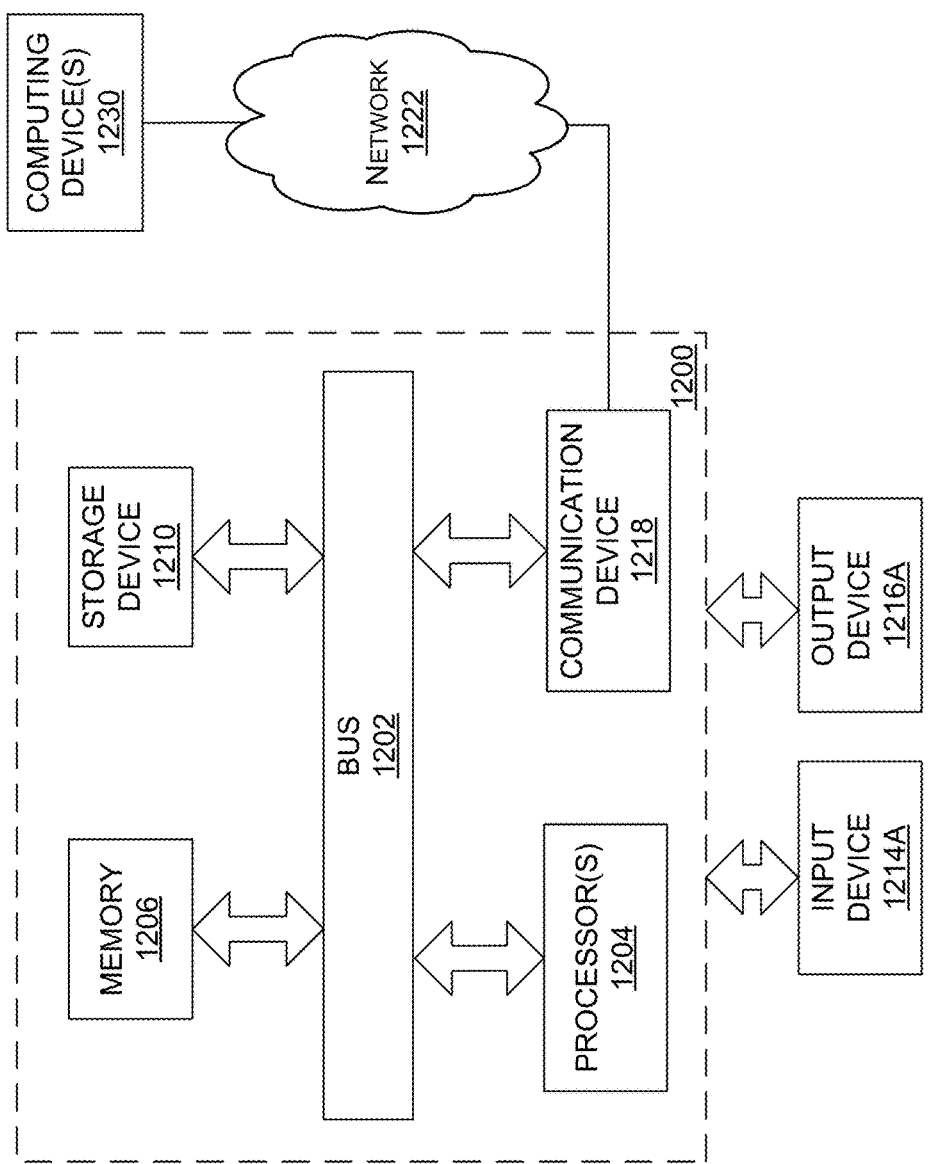
FIG. 12 is a diagram illustrating a computing system with which certain embodiments discussed herein may be implemented.

FIG. 12 depicts a general architecture of a computing system 1200 (sometimes referenced herein as a user computing device, server, and/or computing device). Computing system 1200 and/or components of computing system 1200 may be implemented by any of the devices and/or components discussed herein, such as user computing device 102, one or more providers 104, the communication interface 114, and/or the transformation system 100 of FIG. 1. The general architecture of the computing system 1200 depicted in FIG. 12 includes an arrangement of computer hardware and software components that may be used to implement aspects of the present disclosure. The computing system 1200 may include many more (or fewer) elements than those shown in FIG. 12. It is not necessary, however, that all of these elements be shown in order to provide an enabling disclosure. As illustrated, the computing system 1200 includes one or more hardware processors 1204, a communication interface 1218, a computer readable medium storage and/or device 1210, one or more input devices 1214A (such as a touch screen, mouse, keyboard, etc.), one or more output devices 1216A (such as a monitor, screen, and/or display), and memory 1206, some of which may communicate with one another by way of a communication bus 1202 or otherwise. The communication interface 1218 may provide connectivity to one or more networks or computing systems. The hardware processor(s) 1204 may thus receive information and instructions from other computing systems or services via the network 1222.

The memory 1206 may contain computer program instructions (grouped as modules or components in some embodiments) that the hardware processor(s) 1204 executes in order to implement one or more embodiments. The memory 1206 generally includes RAM, ROM and/or other persistent, auxiliary or non-transitory computer-readable media. The memory 1206 may store an operating system that provides computer program instructions for use by the hardware processor(s) 1204 in the general administration and operation of the computing system 1200. The memory 1206 may further include computer program instructions and other information for implementing aspects of the present disclosure. In addition, memory 1206 may include or communicate with storage device 1210. A storage device 1210, such as a magnetic disk, optical disk, or USB thumb drive (Flash drive), etc., is provided and coupled to bus 1202 for storing information, data, and/or instructions.

Memory 1206 also may be used for storing temporary variables or other intermediate information during execution of instructions to be executed by hardware processor(s) 1204. Such instructions, when stored in storage media accessible to hardware processor(s) 1204, render computer system 1200 into a special-purpose machine that is customized to perform the operations specified in the instructions.

In general, the word "instructions," as used herein, refers to logic embodied in hardware or firmware, or to a collection of software modules, possibly having entry and exit points, written in a programming language, such as, but not limited to, Java, Scala, Lua, C, C++, or C#. A software module may be compiled and linked into an executable program, installed in a dynamic link library, or may be written in an interpreted programming language such as, but not limited to, BASIC, Perl, or Python. It will be appreciated that software modules may be callable from other modules or from themselves, and/or may be invoked in response to detected events or interrupts. Software modules configured for execution on computing devices by their hardware processor(s) may be provided on a computer readable medium, such as a compact disc, digital video disc, flash drive, magnetic disc, or any other tangible medium, or as a digital download (and may be originally stored in a compressed or installable format that requires installation, decompression or decryption prior to execution). Such software code may be stored, partially or fully, on a memory device of the executing computing device, for execution by the computing device. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules or computing device functionality described herein are preferably implemented as software modules, but may be represented in hardware or firmware. Generally, the instructions described herein refer to logical modules that may be combined with other modules or divided into sub-modules despite their physical organization or storage.

The term "non-transitory media," and similar terms, as used herein refers to any media that store data and/or instructions that cause a machine to operate in a specific fashion. Such non-transitory media may comprise non-volatile media and/or volatile media. Non-volatile media includes, for example, optical or magnetic disks, such as storage device 1210. Volatile media includes dynamic memory, such as main memory 1206. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

Non-transitory media is distinct from but may be used in conjunction with transmission media. Transmission media participates in transferring information between non-transitory media. For example, transmission media includes coaxial cables, copper wire and fiber optics, including the wires that comprise bus 1202. Transmission media can also take the form of acoustic or light waves, such as those generated during radio-wave and infra-red data communications.

Computing system 1200 also includes a communication interface 1218 coupled to bus 1202. Communication interface 1218 provides a two-way data communication to network 1222. For example, communication interface sends and receives electrical, electromagnetic, or optical signals that carry digital data streams representing various types of information via cellular, packet radio, GSM, GPRS, CDMA, WiFi, satellite, radio, RF, radio modems, ZigBee, XBee, XRF, XTend, Bluetooth, WPAN, line of sight, satellite relay, or any other wireless data link.

Computing system 1200 can send messages and receive data, including program code, through the network 1222 and communication interface 1218. A computing system 1200 may communicate with other computing devices 1230, such as an application server, via network 1222.

Computing system 1200 may include a distributed computing environment including several computer systems that are interconnected using one or more computer networks. The computing system 1200 could also operate within a computing environment having a fewer or greater number of devices than are illustrated in FIG. 12.

Other Variations

Embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. In addition, the foregoing embodiments have been described at a level of detail to allow one of ordinary skill in the art to make and use the devices, systems, etc. described herein. A wide variety of variation is possible. Components, elements, and/or steps can be altered, added, removed, or rearranged. While certain embodiments have been explicitly described, other embodiments will become apparent to those of ordinary skill in the art based on this disclosure.

The preceding examples can be repeated with similar success by substituting generically or specifically described operating conditions of this disclosure for those used in the preceding examples.

Depending on the embodiment, certain acts, events, or functions of any of the methods described herein can be performed in a different sequence, can be added, merged, or left out altogether (e.g., not all described acts or events are necessary for the practice of the method). Moreover, in certain embodiments, acts or events can be performed concurrently, e.g., through multi-threaded processing, interrupt processing, or multiple processors or processor cores, rather than sequentially. In some embodiments, the algorithms disclosed herein can be implemented as routines stored in a memory device. Additionally, a processor can be configured to execute the routines. In some embodiments, custom circuitry may be used.

The various illustrative logical blocks and modules described in connection with the embodiments disclosed herein can be implemented or performed by a machine, such as a processing unit or processor, a digital signal processor (DSP), an application specific integrated circuit (ASIC), a field programmable gate array (FPGA) or other programmable logic device, discrete gate or transistor logic, discrete hardware components, logical circuitry, or any combination thereof designed to perform the functions described herein. A processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

Each of the processes, methods, and algorithms described in the preceding sections may be embodied in, and fully or partially automated by, code instructions or software modules executed by one or more computing systems or computer processors comprising computer hardware. The processes and algorithms may be implemented partially or wholly in application-specific circuitry. A software module can reside in RAM memory, flash memory, ROM memory, EPROM memory, EEPROM memory, registers, a hard disk, a removable disk, a CD-ROM, or any other form of computer-readable storage medium known in the art. An exemplary storage medium is coupled to a processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied. Conjunctive language such as the phrase "at least one of X, Y and Z," unless specifically stated otherwise, is otherwise understood with the context as used in general to convey that an item, term, etc. may be either X, Y or Z. Thus, such conjunctive language is not generally intended to imply that certain embodiments require at least one of X, at least one of Y and at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to various embodiments, it will be understood that various omissions, substitutions, and changes in the form and details of the devices or algorithms illustrated can be made without departing from the spirit of the disclosure. Although the disclosure has been described in detail with particular reference to the embodiments disclosed herein, other embodiments can achieve the same results. Variations and modifications of the present disclosure will be obvious to those skilled in the art and it is intended to cover all such modifications and equivalents. As will be recognized, certain embodiments described herein can be embodied within a form that does not provide all of the features and benefits set forth herein, as some features can be used or practiced separately from others. The scope of protection is indicated by the claims that may follow rather than by the foregoing description. All changes which come within the meaning and range of equivalency of the claims that may follow are to be embraced within their scope. Accordingly, the present disclosure is not intended to be limited by the recitation of the various embodiments.

What is claimed is:

1. A system for collecting and sharing data from multiple disparate data sources, the system comprising:
   one or more first data stores configured to store a plurality of instruction sets for processing data, wherein each instruction set of the plurality of instruction sets corresponds to a workflow from a plurality of workflows;
   a plurality of second data stores comprising a NoSQL database and a search engine; and
   one or more hardware computer processors programmed, via executable code instructions, to:
      receive, via an application programming interface, original data;
      store the original data in a data store of the plurality of second data stores;
      determine that the original data is incomplete;
      in response to determining that the original data is incomplete, add the original data to a queue;
      receive first data;
      determine that the first data completes the original data;
      generate, from the original data and the first data, second data according to an instruction set;
      store the second data in the data store;
      identify, from the plurality of instruction sets, a first instruction set from a first workflow;
      generate, from the second data, third data according to the first instruction set from the first workflow, wherein generating the third data according to the first instruction set further comprises a first plurality of steps, and wherein the first plurality of steps comprise:
         ingesting the second data into a data object; and
         executing a formatter that takes the data object as an input and outputs the third data;
      store the third data in the NoSQL database and the search engine;
      store the first plurality of steps in the data store, wherein the first plurality of steps indicate generation of a new data item from an original data item in the second data;
      identify, from the plurality of instruction sets, a second instruction set from a second workflow;
      determine a second plurality of steps, wherein to determine the second plurality of steps comprises:
         receive an additional step comprising identifying a new field from a second data object;
      generate, from the second data, fourth data according to the second instruction set from the second workflow, the fourth data being different from the third data, wherein generating the fourth data according to the second instruction set further comprises the second plurality of steps, and wherein the second plurality of steps comprise:
         ingesting the second data into the second data object;
         identifying the new field from the second data object that corresponds to the additional step; and
         executing the formatter that takes the second data object as an input and outputs the fourth data comprising the new field;
      store the fourth data in the NoSQL database and the search engine;
      receive, from a first external computing device, a first request;
      in response to receiving the first request, retrieve the third data from the NoSQL database;
      transmit the third data to the first external computing device;
      receive, from a second external computing device, a second request;
      in response to receiving the second request, retrieve the fourth data from the search engine; and
      transmit the fourth data to the second external computing device.

2. The system of claim 1, wherein respective groups of the first plurality of steps indicate individual transformations of the second data to respective new data items.

3. The system of claim 1, wherein the one or more hardware computer processors are further programmed, via the executable instructions, to:
   add a third workflow to the plurality of workflows, the third workflow comprising a third instruction set for processing data;
   generate, from the second data, fifth data according to the third instruction set; and
   store the fifth data in the NoSQL database and the search engine.

4. A system for collecting and sharing data from multiple disparate data sources, the system comprising:
   one or more data stores configured to store a plurality of instruction sets for processing data; and
   one or more hardware computer processors programmed, via executable code instructions, to:
      receive, via an application programming interface, original data;
      store the original data in the one or more data stores;
      determine that the original data is incomplete;
      in response to determining that the original data is incomplete, add the original data to a queue;
      receive first data;
      determine that the first data completes the original data;
      generate, from the original data and the first data, second data according to an instruction set;
      store the second data in the one or more data stores;
      identify, from the plurality of instruction sets, a first instruction set;
      generate, from the second data, third data according to the first instruction set, wherein generating the third data according to the first instruction set further comprises a first plurality of steps, and wherein the first plurality of steps comprise:
         ingesting the second data into a data object; and
         executing a formatter that takes the data object as an input and outputs the third data;
      store the third data in the one or more data stores;
      store the first plurality of steps in the one or more data stores, wherein the first plurality of steps indicate generation of a new data item from an original data item in the second data;
      identify, from the plurality of instruction sets, a second instruction set;

determine a second plurality of steps, wherein to determine the second plurality of steps comprises:
  receive an additional step comprising identifying a new field from a second data object;
  generate, from the second data, fourth data according to the second instruction set, the fourth data being different from the third data, wherein generating the fourth data according to the second instruction set further comprises the second plurality of steps, and wherein the second plurality of steps comprise:
    ingesting the second data into the second data object;
    identifying the new field from the second data object that corresponds to the additional step; and
    executing the formatter that takes the second data object as an input and outputs the fourth data comprising the new field;
  store the fourth data in the one or more data stores;
  receive, from a first external computing device, a first request;
  in response to receiving the first request, transmit the third data;
  receive, from a second external computing device, a second request; and
  in response to receiving the second request, transmit the fourth data.

5. The system of claim 4, wherein respective groups of the first plurality of steps indicate individual transformations of the second data to respective new data items.

6. The system of claim 4, wherein the first instruction set comprises first boolean logic, wherein the one or more hardware computer processors are further programmed, via the executable instructions, to:
  determine that the second data corresponds to a particular type of data; and
  determine, according to the first boolean logic, to generate the third data because the second data corresponds to the particular type of data.

7. The system of claim 4, wherein the plurality of instruction sets further comprises a third instruction set, wherein the third instruction set comprises third boolean logic, wherein the one or more hardware computer processors are further programmed, via the executable instructions, to:
  determine that the second data corresponds to a particular type of data; and
  determine, according to the third boolean logic, to not generate data according to the third instruction set because the second data corresponds to the particular type of data.

8. The system of claim 4, wherein storing the third data in the one or more data stores further comprises:
  storing the third data in a NoSQL database; and
  storing the third data in a search engine.

9. The system of claim 4, wherein each instruction set of the plurality of instruction sets corresponds to a workflow from a plurality of workflows.

10. The system of claim 9, wherein the one or more hardware computer processors are further programmed, via the executable instructions, to:
  add a third workflow to the plurality of workflows, the third workflow comprising a third instruction set for processing data;
  generate, from the second data, fifth data according to the third instruction set; and
  store the fifth data in the one or more data stores.

11. A method for collecting and sharing data from multiple disparate data sources, the method comprising:
  receiving, via an application programming interface, original data;
  storing the original data in one or more data stores;
  determining that the original data is incomplete;
  in response to determining that the original data is incomplete, adding the original data to a queue;
  receiving first data;
  determining that the first data completes the original data;
  generating, from the original data and the first data, second data according to an instruction set;
  storing the second data in the one or more data stores;
  identifying, from a plurality of instruction sets, a first instruction set;
  generating, from the second data, third data according to the first instruction set, wherein generating the third data according to the first instruction set further comprises a first plurality of steps, and wherein the first plurality of steps comprise:
    ingesting the second data into a data object; and
    executing a formatter that takes the data object as an input and outputs the third data;
  storing the third data in the one or more data stores;
  storing the first plurality of steps in the one or more data stores, wherein the first plurality of steps indicate generation of a new data item from an original data item in the second data;
  identifying, from the plurality of instruction sets, a second instruction set;
  determining a second plurality of steps, wherein determining the second plurality of steps comprises:
    receiving an additional step comprising identifying a new field from a second data object;
    generating, from the second data, fourth data according to the second instruction set, the fourth data being different from the third data, wherein generating the fourth data according to the second instruction set further comprises the second plurality of steps, and wherein the second plurality of steps comprise:
      ingesting the second data into the second data object;
      identifying the new field from the second data object that corresponds to the additional step; and
      executing the formatter that takes the second data object as an input and outputs the fourth data comprising the new field;
  storing the fourth data in the one or more data stores;
  receiving, from a first external computing device, a first request;
  in response to receiving the first request, transmitting the third data;
  receiving, from a second external computing device, a second request; and
  in response to receiving the second request, transmitting the fourth data.

12. The method of claim 11, wherein respective groups of the first plurality of steps indicate individual transformations of the second data to respective new data items.

13. The method of claim 11, wherein the first instruction set comprises first boolean logic, further comprising:
  determining that the second data corresponds to a particular type of data; and
  determining, according to the first boolean logic, to generate the third data because the second data corresponds to the particular type of data.

14. The method of claim 11, wherein the plurality of instruction sets further comprises a third instruction set, wherein the third instruction set comprises third boolean logic, further comprising:

determining that the second data corresponds to a particular type of data; and determining, according to the third boolean logic, to not generate data according to the third instruction set because the second data corresponds to the particular type of data.

15. The method of claim 11, wherein storing the first data in the one or more data stores further comprises:

storing the third data in a NoSQL database; and storing the third data in a search engine.

16. The method of claim 11, wherein each instruction set of the plurality of instruction sets corresponds to a workflow from a plurality of workflows.

17. The method of claim 11, further comprising:

adding a third workflow to the plurality of workflows, the third workflow comprising a third instruction set for processing data;

generating, from the second data, fifth data according to the third instruction set; and storing the fifth data in the one or more data stores.

* * * * *